United States Patent
Beissel et al.

(10) Patent No.: US 9,149,606 B2
(45) Date of Patent: Oct. 6, 2015

(54) ENHANCED INTRODUCER ASSEMBLY

(71) Applicants: Jason Ryan Beissel, Bernville, PA (US); Todd Raymond Hilbert, Shillington, PA (US)

(72) Inventors: Jason Ryan Beissel, Bernville, PA (US); Todd Raymond Hilbert, Shillington, PA (US)

(73) Assignee: TELEFLEX MEDICAL INCORPORATED, Research Triangle Park, NC (US)

( * ) Notice: Subject to any disclaimer, the term of this patent is extended or adjusted under 35 U.S.C. 154(b) by 473 days.

(21) Appl. No.: 13/707,827

(22) Filed: Dec. 7, 2012

(65) Prior Publication Data

US 2013/0150793 A1      Jun. 13, 2013

Related U.S. Application Data

(60) Provisional application No. 61/569,139, filed on Dec. 9, 2011.

(51) Int. Cl.
*A61M 5/00*   (2006.01)
*A61M 25/01*  (2006.01)
*A61M 25/00*  (2006.01)
*A61M 25/06*  (2006.01)
*A61M 29/00*  (2006.01)
*A61M 39/06*  (2006.01)

(52) U.S. Cl.
CPC ....... *A61M 25/0105* (2013.01); *A61M 25/0097* (2013.01); *A61M 25/0662* (2013.01); *A61M 29/00* (2013.01); *A61M 25/0668* (2013.01); *A61M 2039/064* (2013.01)

(58) Field of Classification Search
CPC .................. A61M 2039/064; A61M 25/0097; A61M 25/0662; A61M 25/0668
USPC ............................................. 604/171, 164.05
See application file for complete search history.

(56) References Cited

U.S. PATENT DOCUMENTS

| | | |
|---|---|---|
| 6,336,914 B1 | 1/2002 | Gillespie |
| 2008/0243165 A1 | 10/2008 | Mauch et al. |
| 2008/0262430 A1 | 10/2008 | Anderson et al. |
| 2008/0300538 A1 | 12/2008 | Schweikert et al. |
| 2010/0331784 A1 | 12/2010 | Fisher et al. |

*Primary Examiner* — Kevin C Sirmons
*Assistant Examiner* — Deanna K Hall
(74) *Attorney, Agent, or Firm* — Baker & Hostetler LLP

(57) ABSTRACT

Provided is a sheath assembly comprising a dilator hub and sheath hub, configured for coupling by a first movement that combines simultaneous longitudinal and radial movements, followed by a second movement that is substantially radial, and what is also provided is a sheath assembly that comprising a hemostasis valve with a W-slit.

12 Claims, 20 Drawing Sheets

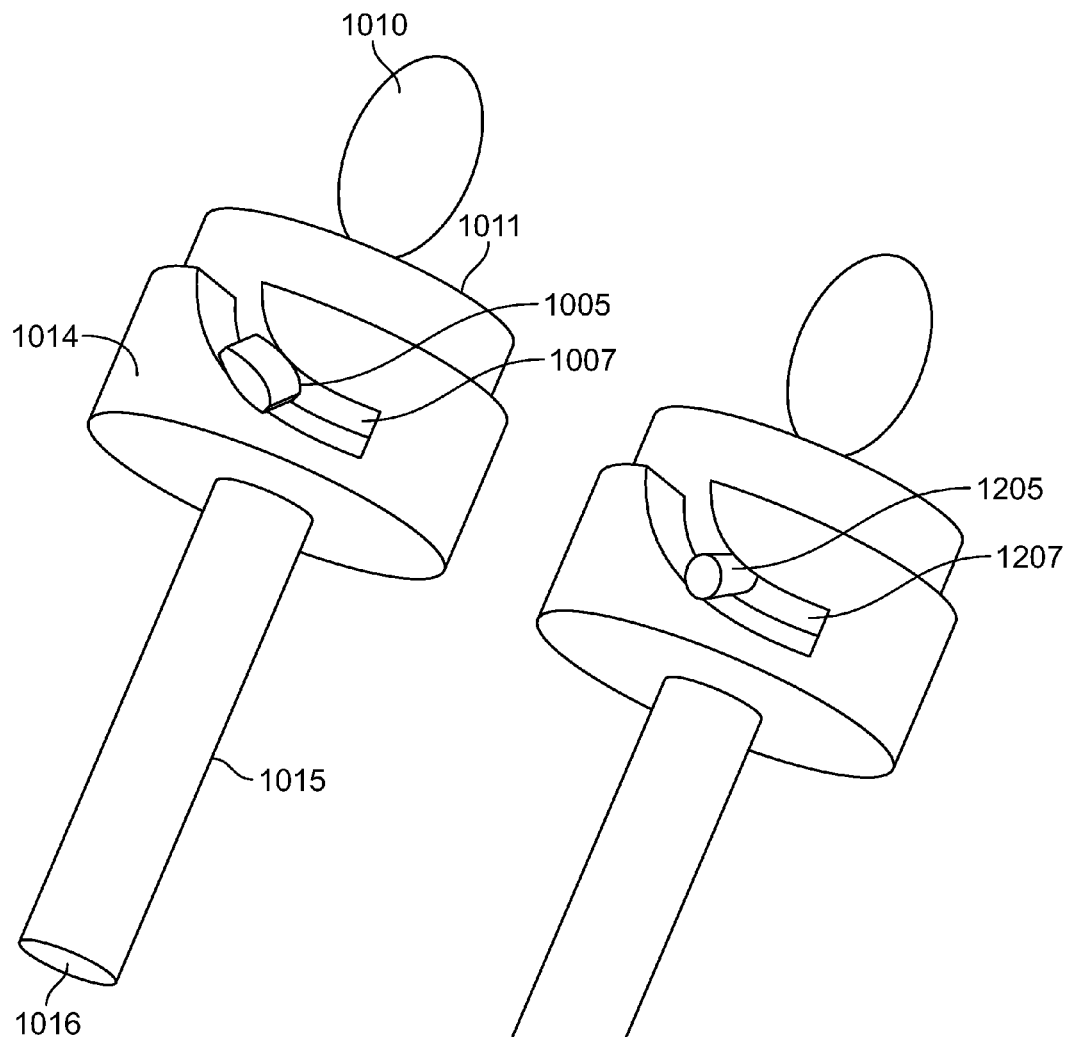
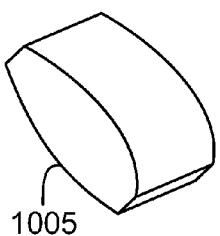
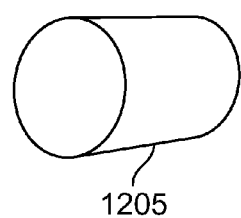
FIG. 1B
FIG. 1C
FIG. 1D
FIG. 1E

ENHANCED INTRODUCER ASSEMBLY

This application claims benefit of priority of U.S. Ser. No. 61/569,139, filed Dec. 9, 2011, and entitled Novel Enhanced Introducer Assembly, which is hereby incorporated herein in its entirety by reference.

FIELD OF THE DISCLOSURE

The present disclosure relates in particular to methods, systems, and devices, for ingress to and egress from sites where patients are treated, whether surgically, interventionally, minimally invasive, or otherwise, dilators and sheaths, and assemblies thereof, as well as to related medical devices such as catheters, needles, and valves.

BACKGROUND OF THE DISCLOSURE

A method for inserting a catheter or vascular sheath into a blood vessel involves the use of the Seldinger technique, which includes an access needle that is inserted into a patient's blood vessel. A guidewire is inserted through the needle and into the vessel. The needle is removed, and a dilator and sheath combination are then inserted over the guidewire. The dilator and sheath combination is then inserted a short distance through the tissue into the vessel. The combination of the needle, dilator, and sheath, can be advanced over the guidewire into the blood vessel. After this combination has been advanced, the dilator is removed. The catheter is then inserted through the sheath into the vessel to a desired location. The Seldinger technique, and variations thereof, and devices used to perform this technique, are described in Seldinger (1953) Acta Radiologica 39:368-376; U.S. Pat. No. 7,722,567 issued to Tal, 7,972,307 issued to Kraus, et al, and 7,938,806 issued to Fisher, et al, which are incorporated by reference. U.S. Pat. No. 6,004,301 issued to Carter provides several elementary diagrams that disclose the insertion of a needle through the patient's flesh, with insertion into a blood vessel. Dilator finds use, for example, to minimize trauma to the patient during insertion of the sheath. Following dilation of the vasculature, dilator is withdrawn and replaced with a desired ancillary medical device, for example, a catheter. Dilator also finds use, where sheath is very flexible, and where the target pathway is very tortuous, and here a dilator is used to facilitate advancing the sheath through the tortuous pathway to the target area (U.S. Pat. No. 7,303,552 of Chu, which is incorporated by reference in its entirety).

If the catheter to be inserted is significantly larger than the guide wire, a sheath (sometimes called "introducer sheath") with a dilator contained inside is passed over the guidewire to enlarge the vessel incision hole. After the incision hole is sufficiently enlarged, the dilator is removed, leaving the sheath and guidewire in position inserted into the incision hole. The guidewire is also usually removed with the dilator. Insertion guidewires are usually not long enough to pass the catheter over. The catheter may come with a wire stylet as a secondary guidewire. Often, the guidewire is removed with the dilator, that is, the guidewire is not left inserted in the incision hole. The catheter is then inserted into the sheath, through the incision hole and into the blood vessel, and the sheath is then removed from around the exterior of the catheter.

When removing the sheath, and where a catheter or other device needs to remain within the sheath and needs to remain within the blood vessel, removal of the sheath is made possible by using a splittable sheath, sometimes called peelable or tearaway sheath.

The sheath that can be split away from the catheter as the sheath is being removed from the patient greatly facilitates the removal of the sheath. By splitting the sheath along its longitudinal axis as the sheath is being removed from the patient, the practitioner can pull out the sheath in such a way that the sheath can be removed without interfering with the catheter, or with any accessories, fittings, clamps, that are part of the catheter. See, e.g., U.S. Pat. No. 7,938,806 issued to Fisher, et al, which is incorporated herein in its entirety.

Where a sheath includes a hub, the hub serves as a handle (wings; tabs), and as a mating point for the insertion and locking of the dilator device. When the sheath needs to be split apart to be successfully withdrawn from the patient's body while leaving the catheter in place, the hub will also have to be split apart in order to clear the catheter. Sheath splitting is necessary, for example, where the catheter has any encumbrance, such as a hub on its proximal end (see, e.g., U.S. Pat. No. 7,422,571 issued to Schweikert and Nardeo, which is incorporated herein by reference).

A dilator is often used to aid in the insertion of the sheath. The dilator can have a long tubular section, the outside diameter of which can be slightly smaller than the inside diameter of the sheath. The dilator also has a pointed tip on its distal end and a hollow longitudinal passageway running the entire length thereof. The dilator is inserted into the patient's body through the sheath along the guide wire, allowing the distal tip to extend into the incision hole, carefully enlarging it. The dilator is then removed along the guide wire prior to insertion of the catheter along the guide wire and into the sheath. The guidewire is also usually removed with the dilator, as mentioned above. In many clinical situations, the guidewire is removed with the dilator, that is, where the guidewire is not left inserted in the incision hole.

However, after the dilator is removed, and before the catheter is inserted through the sheath, the sheath becomes an open conduit, allowing blood to leak or ooze from the vessel through the sheath or allowing air to be aspirated into the vessel through the sheath, neither of which is desirable. The practitioner conventionally has had to place a thumb or finger over the proximal opening of the sheath to prevent blood loss and air embolism. Alternatively, the device can include a valve for preventing blood loss, air emboli, or exposure to blood borne pathogens. Regarding air emboli, air entry through negative pressure differential can cause a build-up of air bubbles, leading to air embolisms in the ventricle. For example, a valve can be configured to automatically close and seal the opening as soon as the dilator is removed. The valve can seal around the guidewire, dilator, and catheter, as well as cause a seal where the sheath does not contain any other medical device. Valve finds use, e.g., where blood pressure makes backflow of blood through the sheath a problem (U.S. Pat. No. 7,303,552 to Chu, which is incorporated herein in its entirety).

Following insertion of the sheath and removal of the dilator, the sheath body forms a conduit for inserting a catheter or other medial articles.

SUMMARY OF THE DISCLOSURE

Briefly stated, the disclosure provides a sheath assembly comprising a dilator hub and sheath hub, configured for coupling by a first movement that combines simultaneous longitudinal and radial movements, followed by a second movement that is substantially radial, and what is also provided is a sheath assembly that comprising a hemostasis valve with a W-slit.

What is provided is sheath assembly comprising a sheath and a tubular member, wherein the tubular member comprises a dilator, cannula, or catheter, said sheath assembly having a first hub (dilator hub) and a sheath having a second hub (sheath hub), comprising, in combination: the dilator hub the comprises a first tubular member that defines a first longitudinal axis; wherein the first tubular member has a first inner diameter and a first outer diameter; the sheath hub comprises a second tubular member that defines a second longitudinal axis; wherein the second tubular member has a second inner diameter and a second outer diameter; wherein the dilator hub comprises a grip that is adapted to be grasped by a finger and thumb; wherein the dilator hub comprises a first coupler and the sheath hub comprises a second coupler, wherein the combination of the first and second couplers comprises a reversible couple; wherein: (a) the dilator hub comprises at least one protrusion that extends radially outwards with respect to the first longitudinal axis, and the sheath hub comprises at least one channel, wherein the at least one protrusion and the at least one channel are configured to rotatingly couple with each other, or (b) the sheath hub comprises at least one protrusion that extends radially inwards with respect to the second longitudinal axis, the dilator hub comprises at least one channel, wherein the at least one protrusion and at least one channel are configured to rotatingly couple with each other, and wherein the channel extends in an arc having a predetermined number of degrees, and wherein the channel is configured as a guide that guides the dilator hub to move rotatably in said arc, and also configured as a guide that guides the dilator hub to move in a proximal-to-distal direction along the longitudinal axis, as determinable by holding the sheath hub in a stationary position and concurrently rotating the dilator hub.

Also provided is the above sheath assembly, wherein the dilator hub comprises at least one protrusion that extends radially outwards with respect to the first longitudinal axis, and the sheath hub comprises at least one channel, wherein the at least one protrusion and the at least one channel are configured to rotatingly couple with each other.

What is also embraced is the above sheath assembly, wherein the sheath hub comprises at least one protrusion that extends radially inwards with respect to the second longitudinal axis, the dilator hub comprises at least one channel, wherein the at least one protrusion and at least one channel are configured to rotatingly couple with each other.

Also contemplated is the above sheath assembly, wherein the protrusion comprises at least one ridge, at least one fin, at least one panel, or at least one male thread. Also provided is the above sheath assembly, wherein the protrusion comprises only one ridge, only one fin, only one panel, or only one male thread.

The following provides exclusionary embodiments. Also provided is the above sheath assembly, wherein the protrusion does not comprise a dome or hemisphere, wherein the dilator hub comprises the at least one protrusion and the sheath hub does not comprise the at least one protrusion, and wherein the channel does not comprise a transition point. In yet another exclusionary embodiment, what is provided is the above sheath assembly, wherein the sheath and catheter, or the sheath and dilator, are not coupled to each other, and are both contained by a first package.

Also embraced is the above sheath assembly, wherein the first coupler and second coupler are couplingly engaged with each other. In an exclusionary embodiment, what is provided is the above sheath assembly, wherein the first coupler and second coupler are not couplingly engaged with each other.

In another embodiment, what is provided is the above sheath assembly, wherein maximal insertion of dilator or catheter into sheath can be accomplished by transit of the protrusion through the channel, wherein transit to achieve maximal insertion of dilator or catheter into sheath requires a rotation of X degrees (X°), wherein the rotation is measurable by relative rotation of dilator or catheter with respect to sheath. Also provided is the above sheath assembly, wherein the transit during insertion and assembly comprises a sequential first transit and second transit, wherein the traverse through the first transit is distinguished from transit through the second transit by an inflection point or by the central location of an inflection region, wherein the rotation during first transit is about 0.5 X maximally possible degrees of rotation, and wherein the rotation during the second transit is also about 0.5 X maximally possible degrees of rotation.

Also provided is the above sheath assembly, wherein in use, the sheath assembly is configured so that there is a longitudinal movement of dilator hub towards sheath hub, wherein longitudinal movement of dilator hub towards sheath hub during first transit is greater than longitudinal movement of dilator or sheath towards sheath during second transit.

What is further provided is the above sheath assembly, wherein maximal insertion and assembly of dilator into sheath can be accomplished by transit of the protrusion through the channel, wherein transit to achieve maximal insertion requires a rotation of X degrees (X°), wherein the rotation is measurable by relative rotation of dilator with respect to sheath, and wherein transit of the protrusion through the channel through the entire X degrees does not involve an inflection point in the channel and does not involve a knee in the channel.

In yet another aspect, what is provided is the above sheath assembly, wherein hub of dilator comprises the at least one or more protrusions, wherein the one or more protrusions extend outward radially from the hub, wherein maximal insertion and assembly of dilator into sheath is effected by transit of the one or more protrusion through the channel, wherein transit to achieve maximal insertion requires a rotation of X degrees (X°), wherein angle X of rotation to achieve maximal insertion is not greater than 180 degrees.

What is also provided is the above sheath assembly, wherein the first hub and second hub are configured to require, in use, a rotating movement for coupling, wherein the rotating movement is the first hub relative to the second hub, and wherein the first hub and second hub are also configured to require a longitudinal movement for coupling to each other, wherein the longitudinal movement is relative to the first and second hub, and wherein with complete coupling during use, essentially every increment of rotating movement is accompanied by an increment of longitudinal movement.

In another aspect, what is provided is the above sheath assembly, wherein the first hub and second hub are configured to require movement that comprises a sequential first transit and a second transit, to effect full coupling, (a) wherein in the first transit the first hub and second hub are configured: to require a rotatable movement for coupling, wherein the rotatable movement is relative to the first hub and second hub, and wherein the first hub and second hub are configured to require a longitudinal movement, wherein the longitudinal movement is relative to the first and second hub, and wherein essentially every increment of rotatable movement is accompanied by an increment of longitudinal movement of hub of dilator and hub of sheath towards each other; and (b) wherein in the second transit the first hub and the second hub are configured: to require a rotatable movement for coupling, wherein the rotatable movement is relative to the first hub and second hub, and wherein the first hub and second hub are configured to allow rotation but to compel a longitudinal movement, wherein the compelled longitudinal movement is relative to the first and second hub, and wherein the compelled longitudinal movement is selected from: (i) Lack of longitudinal movement during rotational movement; and (ii) Longitudinal movement that compels dilator hub and sheath hub to move away from each other, where the compelled longitudinal movement is controlled by a notch.

In another aspect, what is provided is the above sheath assembly, wherein sheath hub comprises a hemostasis valve, and wherein the hemostasis valve comprises a W-slit. Also disclosed, is the above sheath assembly, wherein the sheath is a peel-away sheath, wherein the peel-away sheath comprises a first longitudinal half in operable connection with a second longitudinal half, the first longitudinal half capable of separation and disruption of contact from the second longitudinal half, the sheath further comprising two tear-away wings, the first tear-away wing linked operably connected to the first longitudinal half, the second tear-away wing operably connected to the second longitudinal half, wherein simultaneous application of axial force on the first tear-away wing in opposite vector direction as axial force on second tear-away wing results in partial or complete separation of first longitudinal half from second longitudinal half, wherein the first wing and second wing each comprises a substantially flat proximal surface with sharp edges, wherein the first wing and second wing each comprises a distal surface with substantially curved edges, and wherein the distal surface of each of the first wing and second wing comprises a concave portion that is configured for grasping by a thumbtip or fingertip.

In a valve embodiment, what is provided is a hemostasis valve configured for use in a dilator-sheath assembly, wherein the hemostasis valve comprising a W-slit, wherein the hemostasis valve comprises a proximal face and a distal face, and wherein the hemostasis W-slit is configured to impede the passage of blood from the distal face to the proximal face and to impede the passage of air from the proximal face to the distal face, and wherein the W-slit is further configured to facilitate splitting of the valve. Also provided, is the above hemostasis valve, wherein the valve is configured so that, in use, splitting occurs with fewer wayward split lines, splitting occurs more rapidly, and splitting requires lesser attention to placement of fingers and thumb, as determinable by comparing splitting characteristics with the W-slit valve as described above, and a comparator Y-slit valve.

What is also provided is the above sheath assembly, comprising a sheath and a tubular member, wherein the tubular member comprises a dilator, cannula, or catheter, further comprising a hemostasis valve configured for use in said sheath assembly, wherein the hemostasis valve comprising a W-slit, wherein the hemostasis valve comprises a proximal face and a distal face, and wherein the hemostasis W-slit is configured to impede the passage of blood from the distal face to the proximal face and to impede the passage of air from the proximal face to the distal face, and wherein the W-slit is further configured to facilitate splitting of the valve. Also provided is the above sheath assembly, comprising a sheath and a tubular member, wherein the tubular member comprises a dilator, cannula, or catheter, further comprising a hemostasis valve that has a plurality of holes, wherein the holes are configured to reduce surface tension when inserting dilator, and are configured to provide a sense of softer insertion feel to the user, further comprising (i) an inner seal, wherein the inner seal is configured to provide a circumferential seal around inserted dilator, (ii) an outer seal valve that provides a seal when dilator is not inserted, (iii) a secondary seal configured for pivoting up and down; (iv) a middle cavity configured to allow secondary seal to pivot up and down, as dilator is inserted or retracted; (v) a through-hole configured to allow passing of a dilator, where through-hole is defined by secondary seal.

In another aspect, what is provided is the above sheath assembly, where the sheath is splittable and where the sheath does not comprise a valve. Also provided, is the above sheath assembly, where the sheath is splittable, and where the sheath comprises a splittable valve.

Manufacturing embodiments are also provided. The disclosure encompasses the manufacture of the above sheath and the above tubular member, for example, where the tubular member is dilator, where manufacture comprises couplingly assembling the sheath and tubular member, or wherein manufacture comprises packaging the sheath and tubular member but not coupling.

Methods of use embodiments are additionally provided. What is provided is a method of inserting the above sheath assembly into a subject, comprising inserting coupled dilator and sheath into a subject, followed by uncoupling dilator from sheath, and withdrawing dilator either partially or fully from sheath. In another method of use embodiment, what is further provided is the step of splitting the sheath, where the sheath is splittable.

According to embodiments, there is disclosed a sheath assembly comprising a dilator or catheter having a first hub and a sheath having a second hub, comprising, in combination: the first hub comprises a first tubular member that defines a first longitudinal axis; wherein the first tubular member has a first inner diameter and a first outer diameter; the second hub comprises a second tubular member that defines a second longitudinal axis; wherein the second tubular member has a second inner diameter and a second outer diameter; wherein the first hub comprises a grip that is adapted to be grasped by a finger and thumb; wherein the first hub comprises a first coupler and the second hub comprises a second coupler, wherein the combination of the first and second couplers comprises a reversible couple; wherein the first coupler of the first hub comprises at least one ridge that extends radially outwards with respect to the first longitudinal axis, wherein the second coupler of the second hub comprises a channel or groove, wherein the channel or groove is configured to rotatably engage and couplingly engage the at least one ridge; and wherein the channel or groove extends in an arc having a predetermined number of degrees, and wherein the channel or groove is configured to require the first hub to move rotatably in said arc, and also to require the first hub to move in a proximal-to-distal direction along the longitudinal axis, where the second hub is held in a stationary position. Moreover, what is provided is the above sheath assembly, wherein the first coupler and second coupler are couplingly engaged with each other. In another aspect, what is disclosed is the above sheath assembly, wherein the first coupler and second coupler are not couplingly engaged with each other. Additionally, what is contemplated is the above sheath assembly, wherein the first hub comprises a male member and the second hub comprises a female member, wherein the male member is configured for fitting into the female member, and wherein said fitting is required for coupling engagement. Furthermore, what is embraced is the above sheath assembly, wherein the first hub comprises a female member and the second hub comprises a male member, wherein the male member is configured for fitting into the female member, and wherein said fitting is required for coupling engagement. In yet another embodiment, what is disclosed is the above sheath assembly, wherein the first hub and second hub are configured to require a rotatable movement for coupling, wherein the rotatable movement is relative to the first hub and second hub, and wherein the first hub and second hub are configured to require a longitudinal movement for coupling, wherein the longitudinal movement is relative to the first and second hub, and wherein essentially every increment of rotatable movement is accompanied by an increment of longitudinal movement. Moreover, what is provided is the above sheath assembly, wherein the first hub and second hub are configured to require a first transit and a second transit, to effect full coupling, wherein in the first transit the first hub and second hub are configured: (a) to require a rotatable movement for coupling, wherein the rotatable movement is relative to the first hub and second hub, and wherein the first hub and second hub are configured to require a longitudinal movement, wherein the longitudinal movement is relative to the first and second hub, and wherein essentially every increment of rotatable movement is accompanied by an increment of longitudinal movement; and wherein in the second transit the first hub and the second hub are configured: (b) to require a rotatable movement for coupling, wherein the rotatable movement is relative to the first hub and second hub, and wherein the first hub and second hub are configured to allow rotation but to prevent a longitudinal movement, wherein the prevented longitudinal movement is relative to the first and second hub, and wherein essentially every increment of rotatable movement is not accompanied by any increment of longitudinal movement. In yet another embodiment, what is embraced is the above sheath assembly, wherein the first hub comprises a dilator and wherein the first hub is male, wherein the second hub comprises an introducer sheath and wherein the second hub is female. Also, what is provided is the above sheath assembly, wherein the first hub comprises a dilator and wherein the first hub is female, wherein the second hub comprises an introducer sheath and wherein the second hub is male. Furthermore, what is embraced by the present disclosure is the above sheath assembly, wherein the first hub comprises a dilator, and wherein the first hub further comprises at least one ridge, and wherein the second hub comprises an introducer sheath, and wherein the second hub further comprises a channel or groove, wherein said at least one ridge is configured to couple into said channel or groove, as well as the above sheath assembly, wherein the first hub comprises a dilator, and wherein the first hub further comprises a channel or groove, and wherein the second hub comprises an introducer sheath, and wherein the second hub further comprises at least one ridge, wherein said at least one ridge is configured to couple into said channel or groove. In yet another embodiment, what is provided is the above sheath assembly, wherein the grip has at least one flat face, wherein the first hub, of the dilator or catheter having the first hub, comprises a ridge with a raised profile, wherein the raised profile is measurable in a direction that is substantially perpendicular to the flat face of the grip, and a reduced or flat profile, wherein the reduced or flat profile is measurable in a direction that is substantially parallel to the flat face of the grip.

According to embodiments, the disclosure provides a hemostasis valve configured for use in a dilator-sheath assembly, wherein the hemostasis valve comprising a W-slit, wherein the valve comprises a proximal face and a distal face, and wherein the W-slit is configured to impede the passage of blood from the distal face to the proximal face and to impede the passage of air from the proximal face to the distal face, and wherein the W-slit is further configured to facilitate splitting of the valve. In another aspect, what is provided is the above hemostasis valve, wherein there is a facility of valve splitting, and wherein the facility of valve splitting of the valve with the W-slit is configured to be greater than that of a valve with a Y-slit. Moreover, what is embraces is the above hemostasis valve, further comprising a sheath and a sheath hub, wherein the sheath hub comprises the hemostasis valve; as well as the above hemostasis valve, wherein the sheath comprises at least two wings, wherein the each wing has a proximal face and a distal face, and wherein the proximal face comprises a proximal edge and the distal face comprises a distal edge, wherein the proximal edge is relatively sharp and the distal edge is relatively dull, and wherein the sharp proximal edge is configured to be felt by the thumb, while the dull distal edge is configured to allow wrapping of a finger and to reduce the tearing of a medical glove during use; and additionally the above hemostasis valve, wherein the proximal edge that is relatively sharp has an edge radius of less than $1/1000^{th}$ of an inch, and the distal edge that is relatively dull has an edge radius of greater than $1/100^{th}$ of an inch. In other embodiments, what is contemplated is the above hemostasis valve, wherein the proximal edge that is relatively sharp has an edge radius of less than $1/500^{th}$ of an inch, and the distal edge that is relatively dull has an edge radius of greater than $1/10^{th}$ of an inch. Also disclosed, is the above hemostasis valve, wherein the proximal edge that is relatively sharp has an edge radius of less than $1/2000^{th}$ of an inch, and the distal edge that is relatively dull has an edge radius of greater than $1/10^{th}$ of an inch. In sheath embodiments, what is embraced, is a sheath assembly comprising a dilator or catheter having a first hub and a sheath having a second hub, comprising, in combination: the first hub comprises a first tubular member that defines a first longitudinal axis; wherein the first tubular member has a first inner diameter and a first outer diameter; the second hub comprises a second tubular member that defines a second longitudinal axis; wherein the second tubular member has a second inner diameter and a second outer diameter; wherein the first hub comprises a grip that is adapted to be grasped by a finger and thumb; wherein the first hub comprises a first coupler and the second hub comprises a second coupler, wherein the combination of the first and second couplers comprises a reversible couple; wherein the first coupler of the first hub comprises at least one ridge that extends radially outwards with respect to the first longitudinal axis, wherein the second coupler of the second hub comprises a channel or groove, wherein the channel or groove is configured to rotatably engage and couplingly engage the at least one ridge; and wherein the channel or groove extends in an arc having a predetermined number of degrees, and wherein the channel or groove is configured to require the first hub to move rotatably in said arc, and also to require the first hub to move in a proximal-to-distal direction along the longitudinal axis, where the second hub is held in a stationary position, further comprising, in combination: the above hemostasis valve, or further comprising each of the above-individually disclosed embodiments of the above hemostasis valve.

BRIEF DESCRIPTION OF THE FIGURES

FIG. 1B. Protrusion on dilator hub that is capable of substantially 2-dimensional contact with channel.

FIG. 1C is blowup of panel or fin.

FIG. 1D shows protrusion (pin or pole) on dilator hub that is only capable of 1-dimensional contact with channel.

FIG. 1E is blowup of pin or pole.

Figure 1A:
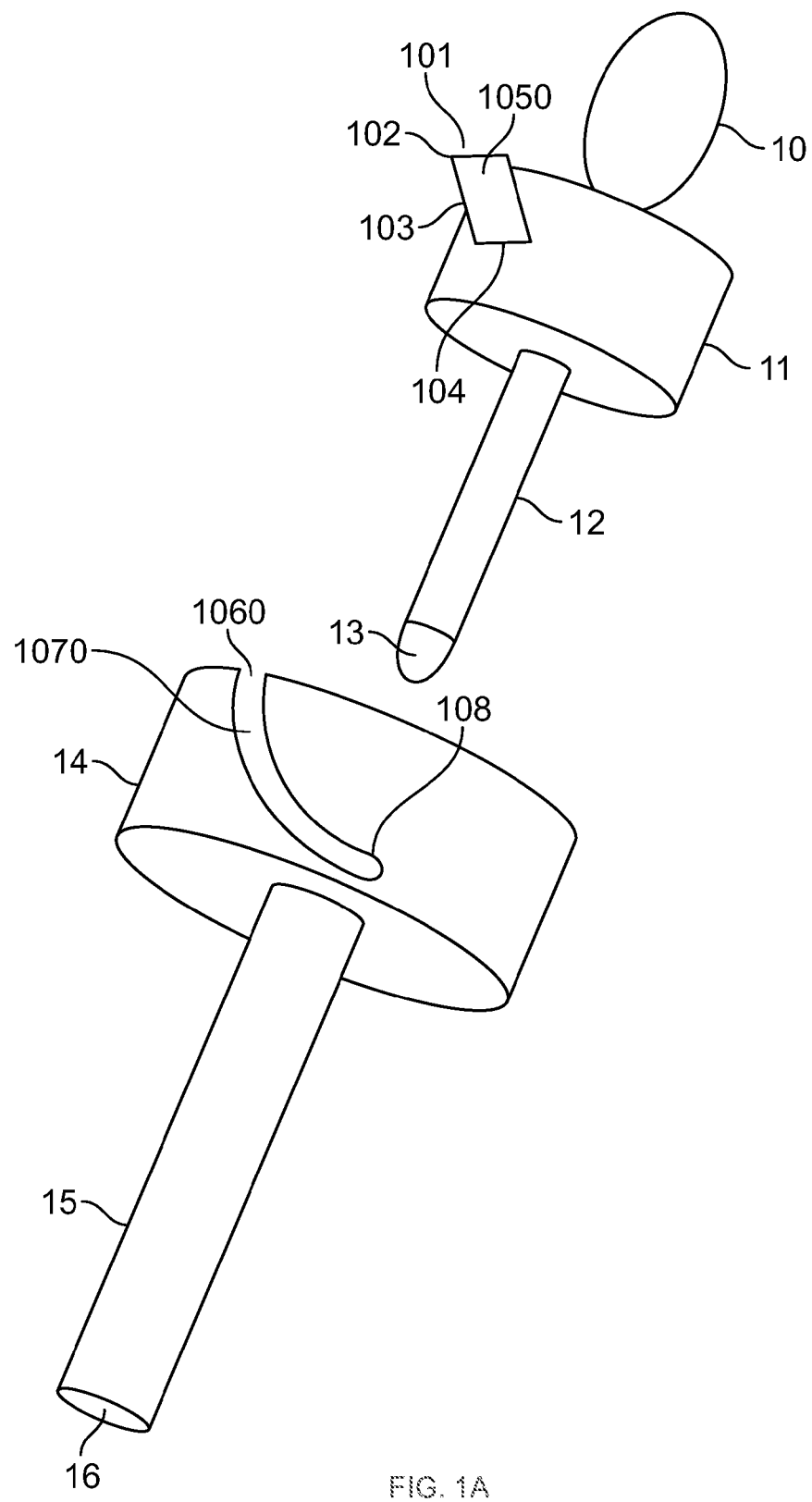
FIG. 1A. Dilator hub (male) and sheath hub (female), where dilator hub comprises an outwardly extending protrusion (e.g., ridge, fin, panel), and sheath hub comprises uncovered groove.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

DETAILED DESCRIPTION OF THE DISCLOSURE

The present inventors offer for consideration improved sheath-dilator apparatus and devices combining the same with valves, whereby trauma to surgical sites is mitigated. In alternative embodiments, where present disclosure provides an assembly that comprises a dilator, e.g., dilator-sheath assembly, what is also provided is an assembly comprising a cannula, catheter, or another type of tubular member in place of the dilator. In other words, what is provided is cannula-sheath assembly, catheter-sheath assembly, tubular member-sheath assembly, and the like. Also provided are other corresponding parts, e.g., cannula hub, catheter hub, and tubular member hub.

Definitions

In the context of a medical device, such a device having a longitudinal aspect, "proximal" refers generally to the end of the device that is closest to the physician while "distal" refers generally to the end that is inserted into the patient. Proximal and distal can be used to refer to sides or positions of devices, such as a sheath, dilator, proximal and distal parts of a dilator tip, dilator-sheath assembly, valve in the context of a sheath, hub in the context of a dilator, hub in the context of a sheath, and so on. Where the terms "proximal-to-distal movement" or "proximal-to-distal force" are used, these terms can refer to the context where the device is being used with the patient, and also in an abstract context, where a physician and patient are not present.

"Complete coupling," in the context of a dilator and sheath, a dilator hub and sheath hub, a catheter and sheath, a catheter hub and sheath hub, a cannula and sheath, a cannula hub and sheath hub, a tubular member and sheath, or a tubular member and sheath hub, refer to the following. Complete coupling refers to optimal coupling, as can be achieved by applying only a rotational force, or as can be achieved by applying only a longitudinal force, or as can be achieved by applying both rotational force and longitudinal force. Optimal coupling can be coupling that results in maximal strength couple, for example, as measurable by applying opposite longitudinal forces that attempt dilator hub from sheath hub. Strength is also measurable by applying vibration to coupled assembly, and determining which coupling position results in maximal stability. Alternatively, optimal coupling refers to maximal depth of insertion of dilator into sheath, for example, where protrusion on dilator hub travels to a maximally obtainable position in channel of sheath hub.

Unless specified otherwise, for example, expressly or by the context, the terms channel, groove, slot, and female thread, encompass a common group of structures.

Unless specified otherwise, for example, expressly or by the context, the term "protrusion" encompasses ridge, fin, male thread, peg, pin, pimple, dome, and the like. In embodiments, a protrusion that is a fin or panel lends greater stability to assembled dilator sheath combination than a protrusion that is a peg, pin, or dome.

"Transit," in the context of a dilator-sheath assembly, or similar device, can refer without limitation to the relative movement longitudinal movement of the dilator and sheath. Relative movement occurs, for example, when the dilator is being inserted into or removed from the sheath. "Transit" can refer to the maximal possible relative movement, for example, the insertion of the dilator entirely into the sheath, that is, until the dilator hub couples with the sheath hub. Also, "transit" can refer to any given part or segment of this movement, where this transit can be delineated in terms of percent maximal insertion or in terms of time taken for a given transit. Additionally, "transit," in the context of the above type of assembly, can refer to rotating movement, that is, movement in an arc, or a combination of rotating movement and longitudinal movement, as might be required or encountered when coupling a dilator hub to a sheath hub, as in hubs that, without intending any limitation, are threaded or contain a Luer lock.

A ridge, tab, fin, pin, peg, or dome (hemisphere), can be part of a sheath hub, dilator hub, catheter hub, and the like, as part of the coupling structure. A ridge, tab, fin, pin, peg, or dome, are not the same as a thread.

Blood that is "upstream" to a device may be "immediately upstream" to the device. Alternatively, blood that is "upstream" to a device is characterized in that the hemoglobin content, oxygen concentration, and carbon dioxide concentration, are essentially the same as blood that contacts the device. In another aspect, blood that is "upstream" to a device is characterized in that no major arteries or veins branch from the vessel in the region between the upstream blood and the device. Without limitation, blood that is "downstream" to a device may be "immediately downstream" to the device. In another non-limiting aspect, blood that is "downstream" to a device is characterized in that the hemoglobin content, oxygen concentration, and carbon dioxide concentration, of the blood are essentially the same as blood that contacts the device. In another aspect, blood that is "downstream" to a device is characterized in that no major arteries or veins branch from the vessel in the region between the downstream blood and the device. The present disclosure can, without limitation, be used for inserting into blood vessels or the heart, into the lymphatics, into cavities containing cerebrospinal fluid, into cavities containing renal filtrate (urological procedures), into the gastrointestinal tract, and the like.

Ridge Embodiments

A ridge is configured to engage rotationally into a groove, where a first hub comprises the ridge, and a second hub comprises the groove, where the dimension of the ridge is less than 50% the full transit dimension of the groove, less than 25% the full transit dimension of the groove, less than 10% the full transit dimension of the groove, and the like. In an alternative ridge embodiment, the ridge is curved in order to facilitate transit of the ridge through a correspondingly curved groove. In yet another ridge embodiment, the ridge is made of a flexible material to facilitate transit of the ridge through a groove that gradually changes its angle, or through a groove that has a substantially longitudinal direction followed by a substantially radial direction, or through a groove that has an angled transit, followed by a purely rotational direction. In embodiments, the ridge is a continuous projection that wraps at least about 5 degrees, at least about 10 degrees, at least about 20 degrees, at least about 30 degrees, at least about 40 degrees, at least about 50 degrees, at least about 60 degrees, at least about 80 degrees, at least about 90 degrees, about the axis. In embodiments, the ridge is less than about 10 degrees, is less than about 20 degrees, is less than about 30 degrees, is less than about 40 degrees, is less than about 50 degrees, is less than about 60 degrees, is less than about 80 degrees, is less than about 90 degrees, or is less than about 120 degrees the axis. In contrast to the present ridge embodiments, a thread is similar to a ridge, except that the thread typically assumes a combined longitudinal dimension and rotational dimension (not just longitudinal; not just rotational). Moreover, a thread is typical helical, that is, it is a continuous projection that wraps helically at least several hundred degrees.

Additional Coupling and Locking Embodiments

With insertion of a first tubular member into a second tubular member, e.g., a dilator into a sheath, or a catheter into a sheath, a coupling mechanism can be configured to allow only a first substantially longitudinal (axial) movement, followed by a second substantially rotating movement, where the second movement completes the act of coupling. In a negative limitation embodiment, the present disclosure excludes a coupling mechanism configured to allow only a first substantially longitudinal (axial) movement, followed by a second substantially rotating movement, where the second movement effects or completes the coupling mechanism. In an angled embodiment, the coupler of the present disclosure excludes embodiments where a ridge moves through a groove, or is guided by a groove, but where any longitudinal (axial) movement is not substantially accompanied by rotational movement. The present coupler, in some embodiments excludes a coupler or lock that requires at least one clip.

French Size

The outside diameter of single lumen catheters is often identified by gauge. The outside diameter of multi-lumen catheters are typically labeled by French size. The disclosure provides a tube (or medical conduit) with a French size that is 3 Fr (1 mm; 0.039 inches), 4 Fr (1.35 mm; 0.053 inches), 5 Fr (1.67 mm; 0.066 inches), 6 Fr (2 mm; 0.079 inches), 7 Fr (2.3 mm; 0.092 inches), 8 Fr (2.7 mm; 0.105 inches), 9 Fr (3 mm; 0.118 inches), 10 Fr (3.3 mm; 0.131 inches), 11 Fr (3.7 mm; 0.144 inches), 12 Fr (4 mm; 0.158 inches), 13 Fr (4.3 mm; 0.170), 14 Fr (4.7 mm; 0.184 inches), 15 Fr (5 mm; 0.197 inches), 16 Fr (5.3 mm; 0.210), 17 Fr (5.7 mm; 0.223 inches), 18 Fr (6 mm; 0.236), 19 Fr (6.3 mm; 0.249), 20 Fr (6.7 mm; 0.263 inches), 22 Fr (7.3 mm; 0.288 inches), 24 Fr (8 mm; 0.315 inches), 26 Fr (8.7 mm; 0.341 inches), 28 Fr (9.3 mm; 0.367 inches), 30 Fr (10 mm; 0.393 inches), and the like. The corresponding diameters in millimeters and inches are shown in parenthesis. The French system has uniform increments between gauge sizes (⅓ of a millimeter) (see, e.g., Iserson K V (1987) J.- F.- B. Charrière: the man behind the "French" gauge. J. Emerg. Med. 5:545-548).

The tube member can comprise, or take the form of, a tubular member, a cylinder, an introducer, a sheath, a shaft, a dilator, a catheter, a needle, and so on. What is provided is a device with exactly the indicated French size, the indicated French size plus or minus 5% the indicated value, plus or minus 10% the indicated value, plus or minus 20% the indicated value, plus or minus 30% the indicated value, and the like. Systems for measuring the outside diameter and inside diameter (lumen) of catheters, needles, and the like have been described (see, e.g., Ahn, et al (2002) Anesth. Analg. 95:1125). French size can refer to an inside diameter or to an outside diameter (see, e.g., U.S. Pat. No. 7,641,645 issued to Schur, which is hereby incorporated by reference).

What is provided is a first tube member configured for fitting inside a second tubular member, where the first tube member has a French size that is about 95% that of the second tube member (comparing outside diameters), about 90% that of the second tube, about 85% that of the second tube, about 80% that of the second tube, approximately 75% that of the second tube, around 70% that of the second tube, about 65% that of the second tube, approximately 60% that of the second tube, around 55% that of the second tube, about 50% that of the second tube, approximately 45% that of the second tube, about 40% that of the second tube, around 35% that of the second tube, and the like. The first tube can comprise a cylinder, an introducer, a sheath, a shaft, a dilator, a catheter, a needle, and so on. The second tube can also be a cylinder, an introducer, a sheath, a shaft, a dilator, a catheter, a needle, and so on. In one embodiment, the first tube is a dilator and the second tube is a sheath.

Sheaths, Dilators, Hubs, Cannulas, Catheters, and Needles

A sheath is generally constructed with a hub at its proximal end. The hub can serve as a mating point for a dilator, as a handle for applying torque, as a grip for holding the instrument, as a grip for applying longitudinal force, as a branching point of tabs or wings for use in splitting a splittable sheath, and as one of the components that is split (when part of a splittable sheath) in order to clear the catheter (see, e.g., U.S. Pat. No. 6,796,991 issued to Nardeo, US2010/0292647 of Nardeo et al, US2009/0143739 of Nardeo, which are incorporated by reference). Where a sheath has a relatively large diameter or has a blunt distal point, a dilator can be used to aid in the insertion of the sheath into the patient. The dilator has a long tubular section, the outside diameter of which is slightly smaller than the inside diameter of the sheath. The dilator has a hollow center which runs along the entire length of the dilator, and the dilator also has a pointed tip on its distal end. A hub can reside on the proximal end of the dilator, where this hub can provide a handle to aid in guiding the dilator into a vessel, and for coupling of the dilator hub to the sheath hub.

Catheter Embodiments

A guidewire can be introduced in a patient's blood vessel, for example, by the Seldinger technique. Once the guidewire is in the blood vessel, a catheter can be threaded over the guidewire, followed by pushing the catheter into the blood vessel. But if the catheter to be inserted is significantly larger than the guidewire, a sheath with a dilator device can be passed over the guidewire to enlarge the vessel incision hole. This is followed by removal of the dilator, and replacement of the dilator with the catheter. After the catheter is pushed into the blood vessel, the sheath is then removed (see, e.g., U.S. Pat. No. 7,938,806 issued to Fisher and Wall). The catheter can be a single lumen catheter or a double lumen catheter, that is, where one lumen introduces fluid and the other lumen removes fluid, or a triple lumen catheter (see, e.g., Barnacle et al (2008) Pediatr. Radiol. 38:363-378). Catheters may comprise, e.g., Teflon®, silicon, or polyurethane. Catheters can be open-ended or valved, and can be coated with an antimicrobial or antithrombotic substance (see, e.g., Gallieni et al (2008) CA Cancer J. Clin. 58:323-346). The catheter may have retractable needles, allowing for local injections (see, Angelini and Bandula (2008) Texas Heart Inst. J. 35:419-424). Catheters, as well as sheaths for introducing catheters, are used for both the arterial (higher pressure) and venous (lower pressure) circulation (see, e.g., U.S. Pat. No. 7,935,102 issued to Breznock et al, which is incorporated herein by reference).

Needle Embodiments

The needle has a needle body and a needle hub. The needle body has a sufficiently long length to access a targeted subcutaneous body space, and has sufficient gauge size to withstand bending or compression forces when being inserted into the patient's body. The inner surface of the dilator shaft may or may not, lie directly against the outer surface of the needle body. Preferably, the annular interface between the outer surface of the needle body and the inner surface of the dilator shaft is minimized to inhibit the flow of blood or other bodily fluids. For many applications, the needle body can have a length of 3-20 cm. The size of the needle is often between 18-26 gauge (see, e.g., US2008/0262430 of Anderson et al). A lock member connects the needle hub to a dilator hub to inhibit relative axial movement between at least a portion of the needle and at least a portion of the dilator, when the lock member is in a locking state. The present disclosure also encompasses a guidewire configured to be axially disposed within at least a portion of the needle body.

Coupler and Lock Embodiments

Coupler embodiments and lock embodiments are provided. Couplers and locks can be non-releasable or they can be reversibly releasable. Unless explicitly stated otherwise, "reversibly releasable" does not mean the same thing as releasable by splitting or tearing, that is by splitting of the sheath, or splitting of the combination of the sheath and hub, and so on.

A coupler or lock of the disclosure connects a dilator to a sheath, connects accessories to sheath, connects accessories to a dilator, connects accessories to a needle or to a needle hub, connects a valve to a sheath, and the like. Couplers involving rotatably engaging studs and complimentary slots, slots in channels, tapered fits, exterior clips, and ring and collar mechanisms, are available (see, e.g., U.S. Pat. No. 6,336,914 issued to Gillespie; U.S. Pat. No. 4,609,370 issued to Morrison; US 2010/0204654 of Mulholland; US 2007/0123825 of King and Wortley; U.S. Pat. No. 6,663,595 issued to Spohn and Dinsmore; US2008/0262430 of Anderson et al; U.S. Pat. No. 5,885,217 of Gisselberg; and US 2005/0090779 of Osypka). Also available are couplers resembling disc brakes (U.S. Pat. No. 7,104,982 issued to McDaniel), couplers resembling clam shell doors on a sheath hub that clamp on a catheter hub (US 2003/0083620 of Luther), and a threaded connector for threadably engaging a locking nut (US 2009/0105652 of Beal and King). Storz-type couplers (U.S. Pat. No. 489,107 issued to Storz are available for medical devices, such as sheaths, dilators, and catheters (see, e.g., U.S. Pat. No. 6,695,816 issued to Casidy. Storz-type couplers are unisex or "sexless" couplers, in contrast to couplers having a male hub and female hub, as stated in U.S. Pat. Nos. 4,648,630 issued to Bruch and 7,128,091 issued to Istre.

Hub embodiments are provided by the present disclosure. The present disclosure encompasses an assembly of a first hub and a second hub, wherein the first hub has a first longitudinal axis and a first radius that is perpendicular to the first longitudinal axis, and wherein the second hub has a second longitudinal axis and a second radius that is perpendicular to the second longitudinal axis, where a coupler is configured to reversibly lock the first hub to the second hub.

Structural Arrangements that Block or Impede Movement of Dilator Relative to Sheath, and Exclusionary Embodiments Thereof.

Movement of dilator, catheter, cannula, and the like (collectively, "dilator"), relative to sheath, can be imposed by the following structural arrangement between dilator and sheath. In sheath assembly, channel can comprises a distal terminus or blind end, where transit of the protrusion (during insertion of dilator) into the channel has a point of maximal transit or insertion. This point of maximal transit or insertion can be defined by one of the following: (a) by contact of the protrusion with the distal terminus or blind end of channel; (b) by contact of hub of dilator or catheter with hub of sheath; or (c) by essentially the simultaneous occurrence of the (a) contact the (b) contact.

In another structural arrangement embodiment, further movement of dilator relative to sheath can be blocked by the following structural arrangement, which involves radial distances. In embodiments, the radial distance from the distalmost part of the channel to the longitudinal axis is greater than the radial distance from the longitudinal axis to the protrusion at a point before the blind end; and, where the radial distance of the bottom of the blind end from the longitudinal axis is equal to or less than the radial distance from the longitudinal axis to the protrusion, so that the male member and female member are inhibited from axial and rotational disengagement when the protrusion resides at the blind end. In an exclusionary embodiment, what is excluded from the present disclosure is the above structural arrangement.

Package Embodiments

The present disclosure provides sheath assembly where the sheath and catheter, or the sheath and dilator, or sheath and tubular member, to provide non-limiting examples, are not coupled to each other (e.g., "couplingly engaged"), and are both contained by a package. Package can be an envelope, a sterile envelope, a bag, a sterile bag, a box, and the like, made of hard plastic, soft plastic, metal, cardboard, and the like, or any combination of these. When in the package, the sheath and tubular member can be pre-assembled, or they can be non-assembled.

Grip Embodiments

Grip embodiments are provided by the present disclosure. The present disclosure encompasses an assembly of a first hub and a second hub, wherein the first hub has a grip configured for grasping by fingers, and where the first hub has a first longitudinal axis and a first radius that is perpendicular to the first longitudinal axis, and wherein the second hub has a second longitudinal axis and a second radius that is perpendicular to the second longitudinal axis, where a coupler is configured to reversibly lock the first hub to the second hub, and wherein rotating the grip is sufficient to effect coupling (without need to apply longitudinal forces that force the first hub in a proximal-to-distal direction and force the second hub in a distal-to-proximal direction, relative to each other).

In a second grip embodiment, what is provided is an assembly of a first hub and a second hub, wherein the first hub has a grip configured for grasping by fingers, first longitudinal axis and a first radius that is perpendicular to the first longitudinal axis, and wherein the second hub has a second longitudinal axis and a second radius that is perpendicular to the second longitudinal axis, where a coupler is configured to reversibly lock the first hub to the second hub, and wherein coupling is effected by applying longitudinal forces that force the first hub in a proximal-to-distal direction and force the second hub in a distal-to-proximal direction, relative to each other (without need to apply rotational forces).

A third grip embodiment, comprises a first relative transit and a second relative transit, where "relative movement" refers to a fixed point on the radius of the first hub and to a fixed point on the radius of the second hub. In this embodiment, coupling involves a first relative transit that is substantially longitudinal (not rotational), where the first hub moves in a proximal-to-distal direction and the second hub moves in a distal-to-proximal direction (relative to each other). Proximal generally means to the side of the physician, while distal means near the side of the patient, without intending any limitation on the present disclosure.

In the third grip embodiment, the first transit is followed by a second transit, where the second transit is substantially rotational (with substantially no relative longitudinal movement), wherein the second transit results in the completion of the locking of the first hub to the second hub. Unlocking requires the reverse of the second transit step followed by reverse of the first transit step. The second transit rotation coupling event can be clockwise, where "clockwise" refers to the perception of the physician viewing the device, where the vector of viewing moves from the physician's eyes to the proximal end of the device, and then continues on to the distal end of the device. Alternatively, the second transit rotation can be counterclockwise.

In a fourth grip embodiment, the first transit involves concurrent rotational and longitudinal movements, where longitudinal force applied at the grip is sufficient to accomplish the entire first transit. The fourth grip embodiment comprises a first relative transit and a second relative transit, where "relative movement" refers to a fixed point on the radius of the first hub and to a fixed point on the radius of the second hub. In the fourth grip embodiment, coupling involves a first relative transit that requires concurrent longitudinal movement and rotational movement, where the first hub moves in a proximal-to-distal direction and the second hub moves in a distal-to-proximal direction (relative to each other). Proximal generally means to the side of the physician, while distal means near the side of the patient, without intending any limitation on the present disclosure.

In a fifth grip embodiment, the first transit involves concurrent rotational and longitudinal movements, where rotational force applied at the grip is sufficient to accomplish the entire first transit. The fifth grip embodiment comprises a first relative transit and a second relative transit, where "relative movement" refers to a fixed point on the radius of the first hub and to a fixed point on the radius of the second hub. In the fifth grip embodiment, coupling involves a first relative transit that requires concurrent longitudinal movement and rotational movement, where the first hub moves in a proximal-to-distal direction and the second hub moves in a distal-to-proximal direction (relative to each to each other).

Where the first transit involves concurrent rotational and longitudinal movements, the entire arc of the transit is at least 5 degrees, at least 10 degrees, at least 15 degrees at least 20 degrees, at least 25 degrees, at least 30 degrees, at least 35 degrees, at least 40 degrees, at least 45 degrees, at least 50 degrees, at least 55 degrees, at least 60 degrees, at least 65 degrees, at least 70 degrees, at least 75 degrees, at least 80 degrees, at least 85 degrees, at least 90 degrees, at least 95 degrees, at least 100 degrees, at least 110 degrees, at least 120 degrees, at least 130 degrees, at least 140 degrees, at least 150 degrees, at least 160 degrees, at least 170 degrees, at least 180 degrees, and the like. The transit can clockwise or counterclockwise, and can be characterized by pausing points, for example, created by bumps that fit into dimples, by mechanical stippling, and the like.

In another aspect, the entire arc of the transit is 1-5 degrees, 5-10 degrees, 10-20 degrees, 15-25 degrees, 20-30 degrees, 25-35 degrees, 30-40 degrees, 35-40 degrees, 40-50 degrees, 45-55 degrees, 50-60 degrees, 55-65 degrees, 60-70 degrees, 65-75 degrees, 70-80 degrees, 75-85 degrees, 80-90 degrees, 85-95 degrees, 90-100 degrees, 100-110 degrees, 110-120 degrees, 120-130 degrees, 130-140 degrees, 140-150 degrees, 150-160 degrees, 160-170 degrees, 170-180 degrees, and the like, as well as any combination of adjacent recitations.

In negative limitation embodiments of the present disclosure, the first transit wherein the first hub is moved in proximal-to-distal direction, and the second hub is moved in a distal-to-proximal direction (relative to each other), and wherein the first transit is in a relative direction that accomplishes coupling, the first transit substantially excludes any movement that is purely in a longitudinal direction, or the first transit substantially excludes any movement that is rotational.

Also, in a negative limitation embodiment, the first transit requires concurrent rotation and longitudinal movement, but where the first transit incapable of a rotation (during the concurrent rotation/longitudinal movement) that is greater than 30 degrees, or greater than 45 degrees, or greater than 60 degrees, or greater than 75 degrees, or greater than 90 degrees, or greater than 105 degrees, or greater than 120 degrees, or greater than 135 degrees, or greater than 150 degrees, or greater than 165 degrees, or greater than 180 degrees, and the like.

Another negative embodiment excludes a thread and excludes threads. The present disclosure provides a sheath hub that is not threaded, and a dilator hub that is not threaded, where the sheath hub and the dilator hub are configured for reversible coupling, wherein the sheath hub and dilator are coupled by a sheath ridge (or pin or tab) that fits into a dilator groove or slot. A ridge that is intermittent is contemplated. Embodiments using one, two, three, or more ridges, tabs, fins, pins, and the like, are contemplated. Male/female embodiments are provided, for example, where the male sheath contains a tab that is configured to reversibly couple with a female groove, and the like. Unisex embodiments, for example, using a Storz-type lock, or a tab and channel type unisex coupling, are also provided.

Exposed and Shielded Embodiments

The disclosure provides a first hub and a second hub, wherein the first hub contains a tab, and the second hub contains a groove configured to couplingly accept the tab, and where the tab has a proximal portion that is permanently attached to the first hub and a distal portion that is configured to substantially enter the second hub's groove. In one aspect, the groove comprises an open aspect that exposes the distal end of the tab when the tab is coupled to the groove. In another aspect, the groove comprises a shielded aspect, shrouded aspect, or covered aspect, that covers the distal end of the tab when the tab is coupled the groove. Also provided are fin embodiments, pin embodiments, thread embodiments, where the fin, pin, or thread is part of the first hub, and where the second hub comprises an open aspect that exposes the distal end of the fin, pin, or thread, or comprises a shielded aspect that covers the distal end of the fin, pin, or thread.

Torque embodiments are contemplated. In one aspect, the present disclosure excludes embodiments that require the user to apply torque for coupling or for locking. In another aspect, the disclosure excludes embodiments that require the user to apply torque for uncoupling or unlocking.

In yet another aspect, what is provided are sweep examples of the concurrent rotational and longitudinal movement embodiment. In a first sweep example, 10 degrees of rotation relative rotation of the first hub to the second hub results in 0.1 mm of relative longitudinal movement (first hub couplingly moving in proximal-to-distal direction and second hub couplingly moving in a distal-to-proximal direction). In a second sweep example, 10 degrees of rotation results in 0.2 mm of relative longitudinal movement. In further sweep examples, 10 degrees of rotation results in 0.4 mm, 0.5 mm, 0.75 mm, 1.0 mm, 1.25 mm, 1.5 mm, 1.75 mm, 2.0 mm, 2.25 mm, 2.5 mm, 2.75 mm, 3.0 mm, 4.0 mm, 5.0 mm of longitudinal movement, and the like. The entire transit of the first transit (or the entire transit of the second transit) can involve a constant sweep ratio (degrees rotation/longitudinal movement). In another aspect, the transit can involve a series (incremental series or smooth series) of sweep ratio, for example, by starting with a steep sweep ratio and ending with shallow sweep ratio, or starting with a shallow sweep ratio and ending with a steep sweep ratio. Negative limitation embodiments of all of the sweep embodiments are provided, that is, where the disclosure excludes one or more of the recited embodiments.

Ratio Embodiments

In some embodiments, ratio is less than 1.0/1.0. In other embodiments, ratio is about 1.0/1.1, about 1.0/1.2, about 1.0/1.3, about 1.0/1.4, about 1.0/1.5, about 1.0/1.6, about 1.0/1.7, about 1.0/1.8, about 1.0/1.9, about 1.0/2.0, about 1.0/2.2, about 1.0/2.4, about 1.0/2.6, about 1.0/2.8, about 1.0/3.0, about 1.0/3.2, about 1.0/3.4, about 1.0/3.6, about 1.0/3.8, about 1.0/4.0, about 1.0/5.0, about 1.0/6.0, about 1.0/7.0, about 1.0/8.0, about 1.0/9.0, about 1/10.0, about 1/15, about 1/20, about 1/25, about 1/30, about 1/40, about 1/50, about 1/60, about 1/70, about 1.0/80, about 1/90, about 1/100, about 1/200, about 1/500, about 1/1000, about 1/2000, about 1/5000, about 1/10000, and so on. In embodiments where the ratio is dramatically different from 1/1, such as where the ratio is about 1/1000, 1/2000, 1/5000, or 1/10000, and the like, the corner with the smaller radius can be reasonably be characterized as a sharp corner. Also encompassed, is a ratio that is in a range that is encompassed by any combination of two of the above ratios.

Male/Female Embodiments

In a first male/female embodiment, the first hub is male and the second hub is female, where the male hub comprises at least one tab, and where the female hub contains a groove that is configured to couplingly accept the tab.

In a second male/female embodiment, the first hub is male and the second hub is female, where the male hub comprises at least one ridge, and where the female hub contains a groove that is configured to couplingly accept the ridge.

In other male/female embodiments, the first hub is not male, but instead is female. In a third male/female embodiment, the first hub is female and the second hub is male, where the male hub comprises at least one tab, and where the female hub contains a groove that is configured to couplingly accept the tab.

In a fifth male/female embodiment, the first hub is female and the second hub is male, where the male hub comprises at least one ridge, and where the female hub contains a groove that is configured to couplingly accept the ridge.

Node Embodiments

The groove can have one or more nodes, where relative movement between the ridge produces regions of increased friction, where each region of increased friction transmits a tactile sensation to the user. Where there is a first groove portion, the first groove portion can have one or more nodes, where relative movement between the ridge and the node produces a region of increased friction during transit through the groove, where the node transmits a tactile sensation to the user. Moreover, where there is a second groove portion the second groove portion can have one or more nodes, where the region of relative movement between the ridge during passage through the groove by each node, constitutes a region of increased friction, where each region of increased friction transmits a tactile sensation to the user.

Valve Embodiments

Valve embodiments are encompassed. What is provided is a hemostatic valve that minimizes blood loss, while allowing optimal movement of the shaft of the catheter (see, e.g., U.S. Pat. No. 5,334,160 issued to Ellis, which is hereby incorporated by reference). The valve prevents fluid from leaving (e.g., bleeding) or from entering the body lumen, when medical instruments or tools are inserted or withdrawn from the valve. Passive valves and active valves are encompassed. The passive valve relies on deformation of a resilient sealing body by the medical instrument being inserted through the valve to form the desired fluid tight seal, while the active valve includes a mechanism that moves a sealing body into contact with the medical instrument being inserted (see, e.g., U.S. Pat. Nos. 7,901,379 and 7,241,276; issued to Argentine et al, which are incorporated by reference). In the valve context, an "opening" can encompass, without limitation, a slit, slot, hole, aperture, access, passage, and the like (see, e.g., U.S. Pat. No. 6,966,896 issued to Kurth et al, which is incorporated herein by reference).

The valve may be reversibly releasable from the sheath, or from the introducer sheath, or it may be an integral part of the device. In one particular valve embodiment, the sheath can be split or partially split without any splitting of the valve, and in this embodiment the valve can have handles that are not the same as the sheath's handles. The valve can be configured for placement over the sheath's outer surface, or for placement at least partially within the passageway of the sheath (see, U.S. Pat. No. 7,101,353, issued to Lui et al, which is incorporated by reference). In a non-limiting splittable embodiment, the valve has scores (fissure lines; grooves) formed nearly all the way through the inside of the valve, outside of the valve, or both inside and outside, such that the two valve halves can be pulled apart when the handles (tabs; wings) of the sheath are pulled apart to initiate the split.

The valve may have a duckbill shape having two flat flaps, where the two flaps extend longitudinally, and where one end of each flap (proximal ends) is connected to an interior side wall of the valve (or an interior side wall of a hub, where the valve is built into a hub), and where the other end of each flap (distal ends) meet and form a tapered tip that forms a slit. The slit is deformed by mechanical force and allows passage of a catheter, dilator, and the like. Inserting a dilator through the valve and through the slit pushes the valve flap ends to the side thereby allowing passage of the dilator. When the dilator is removed, the flexibility of the valve flaps allows the valve to close and reduce the chance of blood loss or air emboli (see, e.g., U.S. Pat. No. 7,938,806 issued to Fisher and Wall, which is incorporated herein by reference). In valve embodiment expressly stated to comprise a "W-slit," the meaning is that valve contains only a W-slit and does not include a Y-slit or any other type of slit, unless dictated otherwise by explicit language or by the context. In valve embodiment expressly stated to comprise a "Y-slit," the meaning is that valve contains only a Y-slit and does not include a W-slit or any other type of slit, unless dictated otherwise by explicit language or by the context.

The present disclosure contemplates a valve that is not integrated with the sheath, for use in the following situation. The physician may need to advance a sheath into a vessel, then partially withdraw the sheath, perhaps 10 cm, prior to introducing a lead through the sheath. Where there is an integral valve at the proximal end of the sheath, this will require an undesirably long section of sheath exiting the patient. Ideally, the physician would like to peel the introducer back closer to the entry site.

A valve that is fitted into the sheath, where the valve can be independently split from the splitting of the sheath, is configured for the situation where the sheath needs to be inserted and then withdrawn somewhat, and then used for inserting the medical device of interest. The medical devices and therapeutic agents used as part of the devices and methods of the present disclosure encompass, without limitation, a lead, a dilation balloon, a stent, an ablation device, an embolic filter, drugs, or radiation sources (see, e.g., U.S. Pat. Nos. 7,582,070 issued to Good et al; 8,016,752, issued to Armstrong et al; and 7,935,108 issued to Baxter, et al; all of which are hereby incorporated by reference). Filters can be used to prevent air emboli (see, e.g., U.S. Pat. No. 7,935,102 issued to Breznock et al, which is incorporated herein by reference). Catheters can be used to deliver or operate these medical devices and therapeutic agents.

Splitting Embodiments

Splitting of a device can be facilitated, guided, or controlled, by a "starter split" or notch (U.S. Pat. No. 7,101,353 issued to Lui and Boyle), by "stress risers" (US2007/0123825 of King et al); by a "bump member" (U.S. Pat. No. 5,885,217 issued to Gisselberg and Hicks); use of specific angles between the general direction of the handle member and the sheath member where the angle produces a fulcrum (U.S. Pat. No. 6,796,991 issued to Nardeo); or a device configured for improved splitting by a combination of twisting forces and pulling forces (US2010/0204654 of Mulholland and Taylor); and use of a splitting tool (U.S. Pat. No. 7,632,254 issued to Bjorkman et al). These patent documents are all incorporated herein by reference. The splitting of the present disclosure can produce two halves, three split thirds, four split quarters, a splintered device, a shattered device, a partially or fully dissolved device, and the like.

What is provided is a medical device comprising a valve, introducer assembly comprising a valve, a sheath comprising a valve, or assembly comprising a sheath and dilator and valve. In each of these embodiments, the valve is splittable or the valve is not splittable. In each of these embodiments the valve comprises frangible web, tear seam, or score line, or does not comprise a frangible web, tear seam, or score line. Where device of the present disclosure has a valve in sheath hub, using a peelaway sheath can facilitate removal of the valve to allow passage of biopsy sample, stone, or other specimen too large to pass through the valve. Also, if there is a proximal fitting (a fitting that is large or cumbersome) that is attached to a cannula residing in the lumen of the sheath, use of peelaway sheath can be broken away, leaving in place that proximal fitting. In other words, if there is this proximal fitting, the peelaway feature of the sheath allows withdrawal of the sheath without need to break apart fitting (U.S. Pat. No. 5,250,033 of Evans, which is incorporated herein in its entirety).

In one aspect, the sheath has only one tear seam, where the tear seam is preferably longitudinal. In another aspect, the sheath has two tear seams, each seam extending in a substantially longitudinal direction aligned with the longitudinal direction of the hollow tube, and each longitudinal seam preferably situated opposite to each other.

Frictional Embodiments

The tubular members of the present disclosure, e.g., dilator and sheath, can be configured to have essentially no friction during passage of the dilator through sheath, or to be configured to have friction where a measurable force is required to overcome the friction. Friction can be measured, e.g., when the dilator is inserted to about 50% the maximal depth of the shaft, and where friction is measured during movement, that is, not from a standing start. In typical embodiments, the present assembly of tubular members is configured to require less than 10 Newtons (N), 5 N, 2 N, 1 N, 0.5 N, 0.2 N, 0.1 N, 0.05 N, 0.02 N, 0.01 N, 0.005 N, 0.002 N, 1 mN, 0.5 mN, 0.2 mN, 0.1 mN, 0.05 mN, 0.02 mN, 0.01 mN, 0.005 mN, 0.002 mN, 0.001 mN, 0.0005 mN, 0.0002 mN, and the like, or to have no measurable friction. In conventional embodiments, the present assembly of tubular members is configured to require at least 10 Newtons (N), 5 N, 2 N, 1 N, 0.5 N, 0.2 N, 0.1 N, 0.05 N, 0.02 N, 0.01 N, 0.005 N, 0.002 N, 1 mN, 0.5 mN, 0.2 mN, 0.1 mN, 0.05 mN, 0.02 mN, 0.01 mN, 0.005 mN, 0.002 mN, 0.001 mN, 0.0005 mN, 0.0002 mN, and the like. One newton (unit of force) is equal to the amount of force required to accelerate a mass of one kilogram at a rate of one meter per second squared. In another aspect, the present assembly of tubular members, when inserted to about 50% maximal depth, is configured to have a coefficient of friction, of less than 4.0, less than 3.5, less than 3.2, less than 3.0, less than 2.5, less than 2.2, less than 2.0, less than 1.5, less than 1.2, less than 1.0, less than 0.9, less than 0.8, less than 0.7, less than 0.6, less than 0.5, less than 0.4, less than 0.3, less than 0.2, less than 0.15, less than 0.12, less than 0.10, less than 0.08, less than 0.07, less than 0.06, less than 0.05, less than 0.04, less than 0.03, less than 0.02, less than 0.01, and the like. In another aspect, the assembly is configured a coefficient of friction that is greater than 0.01, 0.02, 0.03, 0.04, 0.05, 0.06, 0.07, 0.08, 0.09, 0.10, 0.12, 0.15, 0.20, 0.22, 0.25, 0.30, 0.32, 0.35, 0.40, 0.42, 0.45, 0.50, 0.52, 0.55, 0.60, 0.62, 0.65, 0.70, 0.72, 0.75, 0.80, 0.82, 0.85, 0.90, 0.92, 0.95, 1.0, 1.2, 1.5, 2.0, 2.2, 2.5, 3.0, 3.2, 3.5, 4.0, and the like.

Polymer Embodiments

Polymer embodiments are encompassed. The sheath, dilator, catheter, hub, valve, coupler, lock, annulus, or cap, of the present disclosure, can be made of, for example, silicone, rubber, polycarbonate, fluoropolymers, polytetrafluoroethylene (PTFE), fluorinated ethylene propylene (FEP), high density polyethylene.ethylene vinyl Acetate (EVA), nylon or polyamide (PA), polyetheretherketone (PEEK), polyethylene (PE), polypropylene (PP), polytetrafluoroethylene (PTFE), polyurethane (PU), polyvinyl chloride (PVC). Manufacturers of catheters, and expertise in bonding, flanging, tip forming, skiving, are available (Teleflex Medical, Kenosha, Wis.; Becton Dickinson Medical, Franklin Lakes, N.J.; Fluortek, Inc., Easton, Pa.; PlasticWeld Systems, Inc., Newfane, N.Y.). Unless otherwise specified, the present disclosure is not limited to polymers. Ceramics, metals, and so on, are also contemplated.

The present disclosure is configured for improved ergonomics for the physician or nurse. Also, the disclosure minimizes or reduces trauma to the patient, and minimizes or reduces stretching the incision in the skin of the patient. The present disclosure enables the physician to operate the device using only one hand. The device of the present disclosure is configured to prevent confusion with other medical devices, in the context of conducting medical procedures.

The present disclosure, without limitation, can be manufactured with a splittable sheath, as well as with a splittable sheath plus other splittable components, such as a splittable hub, valve, handle, cap, or actuator (see, e.g., US2010/0204654 of Mullholland and Taylor; US2005/0090779 of Osypka; US2007/0123825 of King and Wortley; U.S. Pat. No. 6,796,991 issued to Nardeo; and U.S. Pat. No. 6,336,914 issued to Gillespie). Each of these patent documents is incorporated herein by reference. Components for the methods and devices of the present disclosure are available, for example, from any major medical device company, for example, Medtronic of Minneapolis, Minn.; Advanced Cardiovascular Systems in Santa Clara, Calif.; Baxter International of Deerfield, Ill.; Abbott Laboratories at Abbott Park, Ill., Edwards Lifesciences, Irvine, Calif., and Boston Scientific of Natick, Mass.

EXAMPLES

The disclosure encompasses a valved peel-away version to prevent air entry (air embolism) into the vasculature during negative venous pressure and prevent blood exposure (reflux) during usual positive venous pressure. Worst case, the valve should hold a minimum of 20 mmHg of pressure in either direction for the time of percutaneous access. The first mode of holding pressure is when the device is inserted into the patient over the guide wire assembled with the dilator through the sheath. The second mode is when the dilator is removed and the guide wire is still in place. The third mode is when the guide wire is removed and the sheath is in place with nothing through the valve. The final mode is when the catheter is placed through the sheath. After the catheter is in place, the assembly is peeled and removed.

The disclosure provides a multi-piece valve design. The wings act like a cap which clicks into the nose cone allowing the valve to be pinched/sealed. In a preferred embodiment, there are four male clips on the wing cap which mate with the four openings on the nose cone. This connecting interface is designed so that the peeling axis is 90 degrees transverse from the clips so that once the two halves are peeled apart the half-wing-cap remains clipped to the half-nose cone. A valve interface is contemplated. In one embodiment, the valve interface uses interlocking peaks-and-valleys on both the nose cone and wing cap to pinch the valve. This arrangement allows the valve to be in compression and at the same time in tension when peeling it into halves. In another embodiment, what is used is male pegs with though-holes in the valve. The valve can be one slit (straight slit), Y-slit, asterisk-slit, star-slit, or have a second check-valve which is just a hole which mates tight against the device passing through; since there are three devices of varying diameters. In a preferred embodiment, a check valve may be needed at low pressures and small diameters.

The nose cone of the valve embodiment can hold the guard. The structure whereby the nose cone holds the guard is novel. In the wing hub, the peel groove passes through each ramp to allow the tensile stress to build a single point, where this discontinuous ramp does not affect rotation of the dilator hub in and out of the sheath hub.

FIG. 1A discloses dilator hub (11) (male) and sheath hub (14) (female), where dilator hub (11) comprises outwardly extending protrusion (1050), and sheath hub (14) comprises uncovered groove or channel (107). Grip (10) is at proximal end of dilator hub (11). The numbers at dilator portion refer to grip (10), dilator hub (11), dilator tubular portion (12) and dilator tip (13). Dilator (101) comprises dilator tubular portion and dilator hub (11).

Unless expressly specified, or dictated by the context, the terms ridge, fin, and tab, may be used interchangeably. But generally, a fin has a pointed radial tip, a tab has a square-ended tip, and a ridge is distinguished as having a somewhat longer wrap (measured in degree angles) than a fin or tab.

The numbers at sheath portion refer to sheath hub (14), sheath tubular portion (15), groove (1070) open end of groove (1060), and closed end of groove (108). Leading edge of ridge is (1050), trailing edge of ridge is 103; tip of ridge is 102. Tip of ridge has a length, where the length tracks ridge as ridge wraps around hub, where the length may be referred to as crest length or backbone length. Distal open end of sheath is (16). In this particular drawing, the ridge could also be characterized as a panel.

FIG. 1B protrusion (1005) that is a fin or panel, and that maintains substantial 2-dimensional contact with surface of channel (1007). The substantially 2-dimensional contact is maintained when rotating the dilator (1011) clockwise, or when rotating the dilator counterclockwise, with respect to sheath (1015) Dilator grip (1010), dilator hub (1011), sheath hub (1014), sheath body (1015), and sheath distal tip (1016) are shown.

FIG. 1C is a blow-up of protrusion (1005) that is a fin or panel.

FIG. 1D is a protrusion (1205) that is a pin or pole, and that maintains only 1-dimensional contact with surface of channel (1207).

FIG. 1E is a blow-up of the protrusion (1205) that is a pin or pole.

Figure 2:
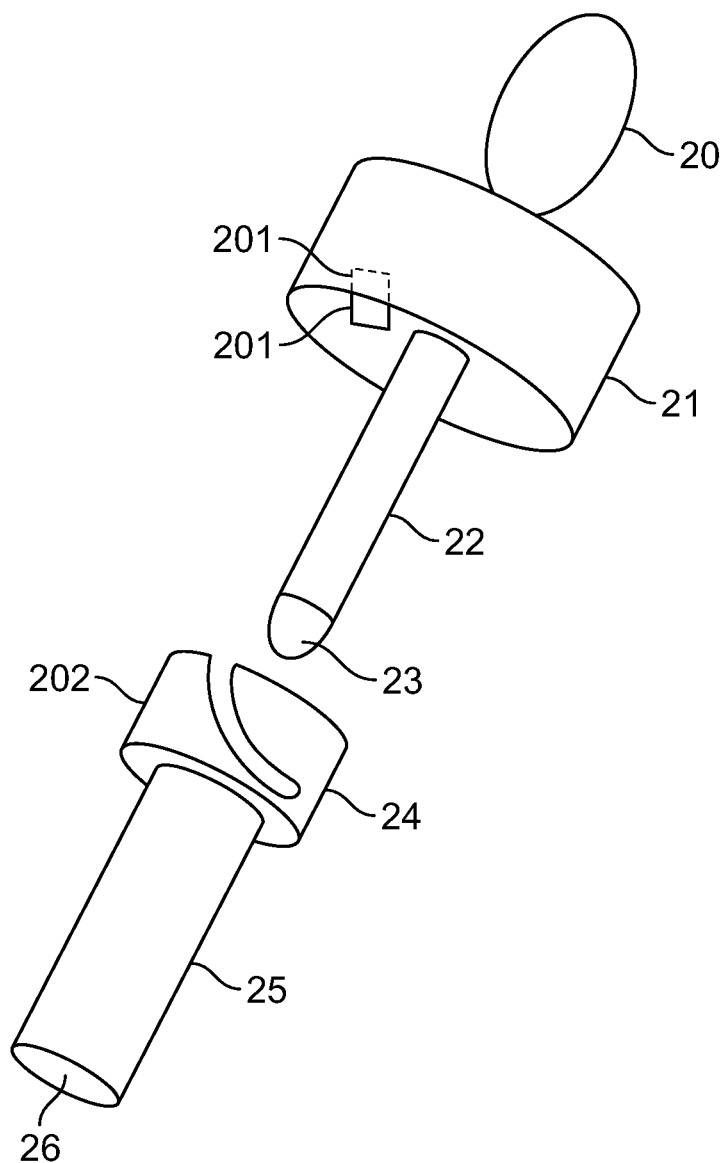
FIG. 2. Dilator hub (female) and sheath hub (male), where dilator hub comprises an inwardly extending ridge, and sheath hub comprises uncovered groove.

FIG. 2 depicts dilator hub (21) (female) and the sheath hub (24) (male), where dilator hub (21) comprises inwardly extending ridge (201), and sheath hub (24) comprises uncovered groove (202). Dilator hub (21) comprises grip (20), where grip (20) resides at proximal end of dilator hub (21). In one aspect, grip (20) is configured to be grasped by a finger and thumb of one hand. In another aspect, grip (20) is configured to be rotated by a grasping finger and thumb of one hand. In yet another embodiment, grip (20) is configured to be held by a finger and thumb of one hand, and pushed in a longitudinal direction, where pushing results in insertion of dilator tubular portion (22) either partially or fully into the sheath (25). Moreover, grip (20) is configured for holding by a finger and thumb of one hand, and for reversing one or more of the above operations. The numbers refer to grip (20), dilator hub (21), dilator tubular portion (22), dilator tip (23), sheath hub (24), sheath tubular portion (25), open end of sheath (26). Coupling mechanism comprises at least one ridge (201), where ridge is inwardly extending inside the dilator hub, and at least one groove (202) in sheath hub. In coupling, ridge (201) rotatingly engages groove (202).

Figure 3:
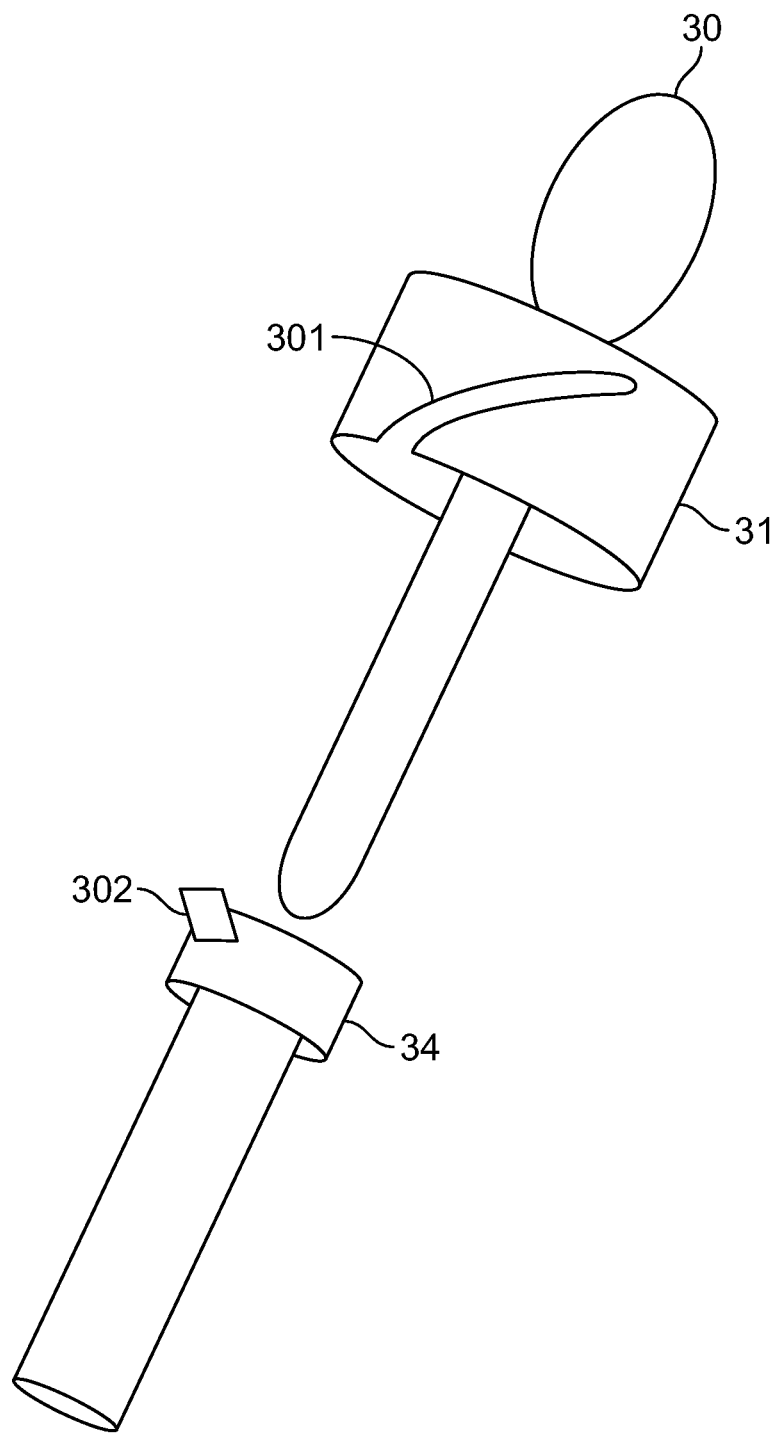
FIG. 3. Dilator hub (female) and sheath hub (male), where dilator hub comprises uncovered groove, and sheath hub comprises outwardly extending ridge.

FIG. 3 shows dilator hub (31) (female) and sheath hub (male) (34), where dilator hub (31) comprises uncovered groove or channel (301), and sheath hub (34) comprises outwardly extending ridge or protrusion (302). A grip (30) is at proximal end of dilator hub.

Figure 4:
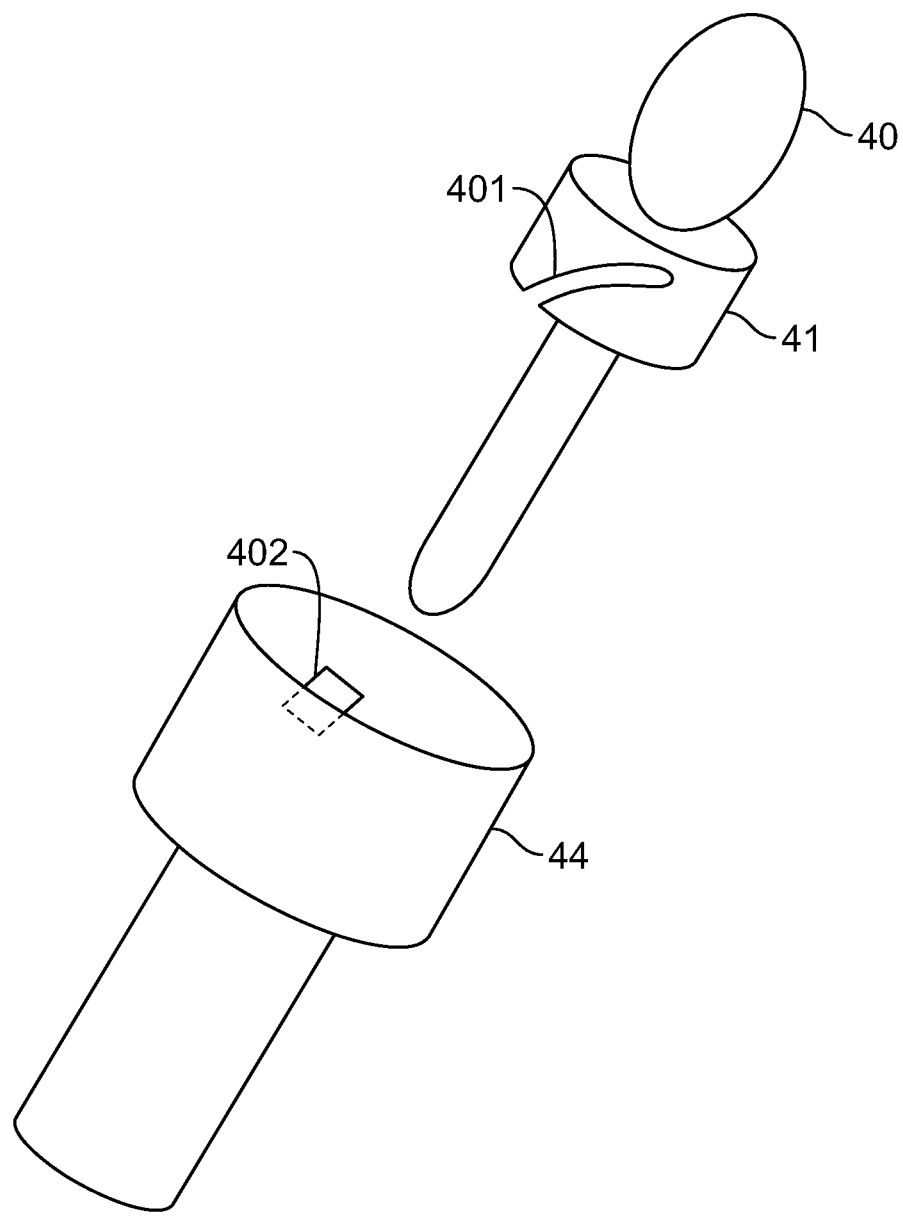
FIG. 4. Dilator hub (male) and sheath hub (female), where dilator hub comprises an uncovered groove, and sheath hub comprises an inwardly extending ridge.

FIG. 4 illustrates dilator hub (41) (male) and sheath hub (44) (female), where dilator hub (41) comprises uncovered groove (401) or channel, and sheath hub (44) comprises inwardly extending ridge (402) or protrusion. Grip (40) is at proximal end of dilator hub.

Figure 5:
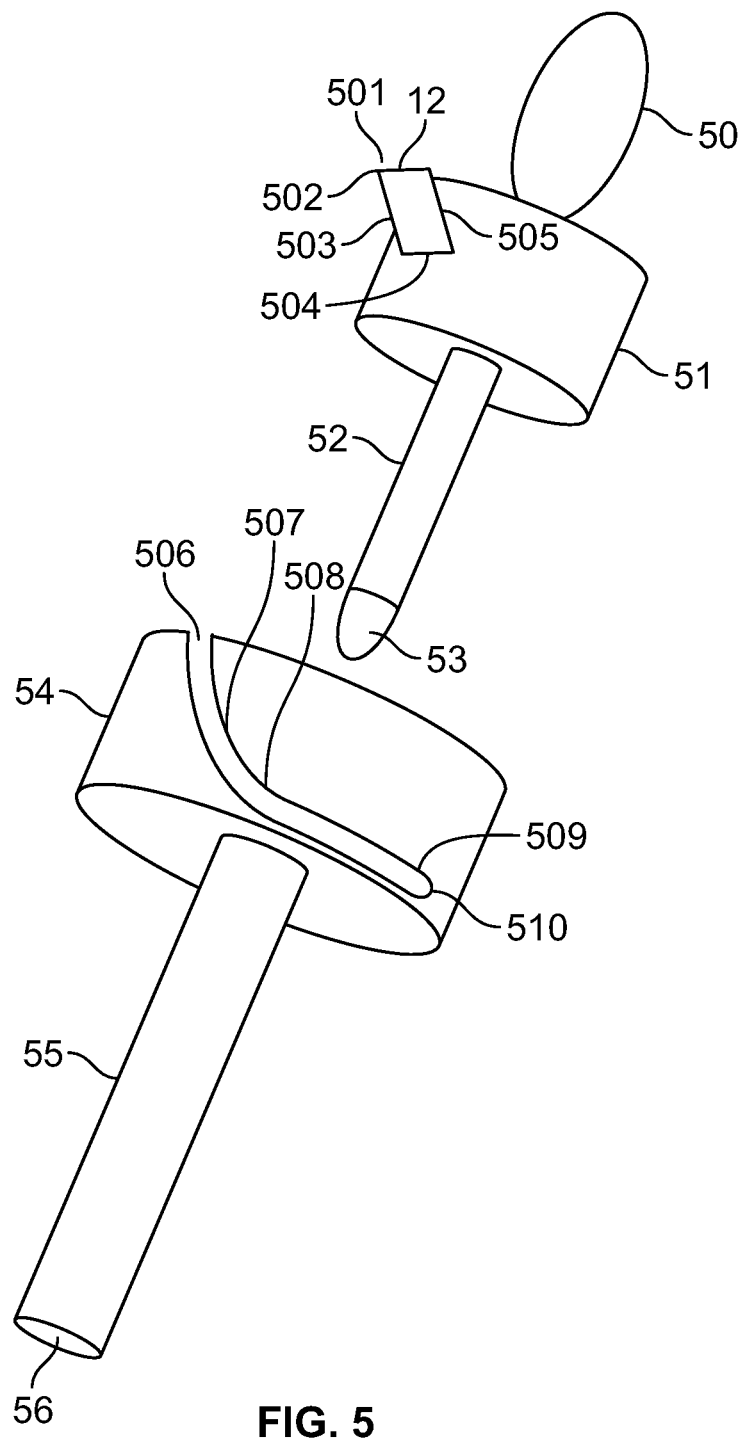
FIG. 5. Dilator hub (male) and sheath hub (female), where dilator hub comprises outwardly extending ridge, and sheath hub comprises uncovered groove comprising first transit groove (or first groove portion), transition or inflection point, and second transit groove (or second groove portion, uncovered helical path).

FIG. 5 reveals grip (50), dilator hub (51) (male) and sheath hub (54) (female), where dilator hub (51) comprises outwardly extending ridge (or protrusion) (503), and the sheath hub (54) comprises uncovered groove (or channel) (506, 507, 508, 509, 510) comprising entry point (506), a first transit groove (507), transition or inflection point (508), second transit groove (509), and terminus (510). In some embodiments, terminus (510) serves to halt rotational movement of grip (50), but in other embodiments rotation causes dilator hub (51) to contact sheath hub (54), where this contact brings rotation to a halt. In other embodiments, rotation is simultaneously brought to halt by contact of protrusion with terminus, and by contact of dilator hub to sheath hub. Dilator body (52), dilator distal tip (53), sheath body (55), and sheath distal tip (56) are also shown.

A grip (50) is situated at the proximal end of the dilator hub (51). First groove portion (507) guides ridge (503) to move concurrently rotatably and longitudinally, that is, in a vector comprising rotating vector and longitudinal vector. With respect to the longitudinal axis, an angle of 90 degrees (referring to angle between groove and longitudinal axis) prevents any longitudinal movement, unless axially-applied force that is applied to grip (or to dilator hub) is great enough to break or fracture sheath hub. Angle in first groove portion (507) can be about 95 degrees, about 100 degrees, about 110 degrees, about 120 degrees, about 130 degrees, about 140 degrees, about 150 degrees, about 160 degrees, about 170 degrees. Angle need not be constant along the entire transit of first groove portion (507), but it can be initiated at a relatively steep angle, e.g., 160 degrees, and then conclude at a relatively shallow angle, e.g., 120 degrees. In embodiments, second groove portion (509) is generally at 90 degrees, relative to the longitudinal axis of the dilator and sheath. This particular angle (90 degrees) allows only rotational movement, and prevents longitudinal movement.

Figures 6, 7A:
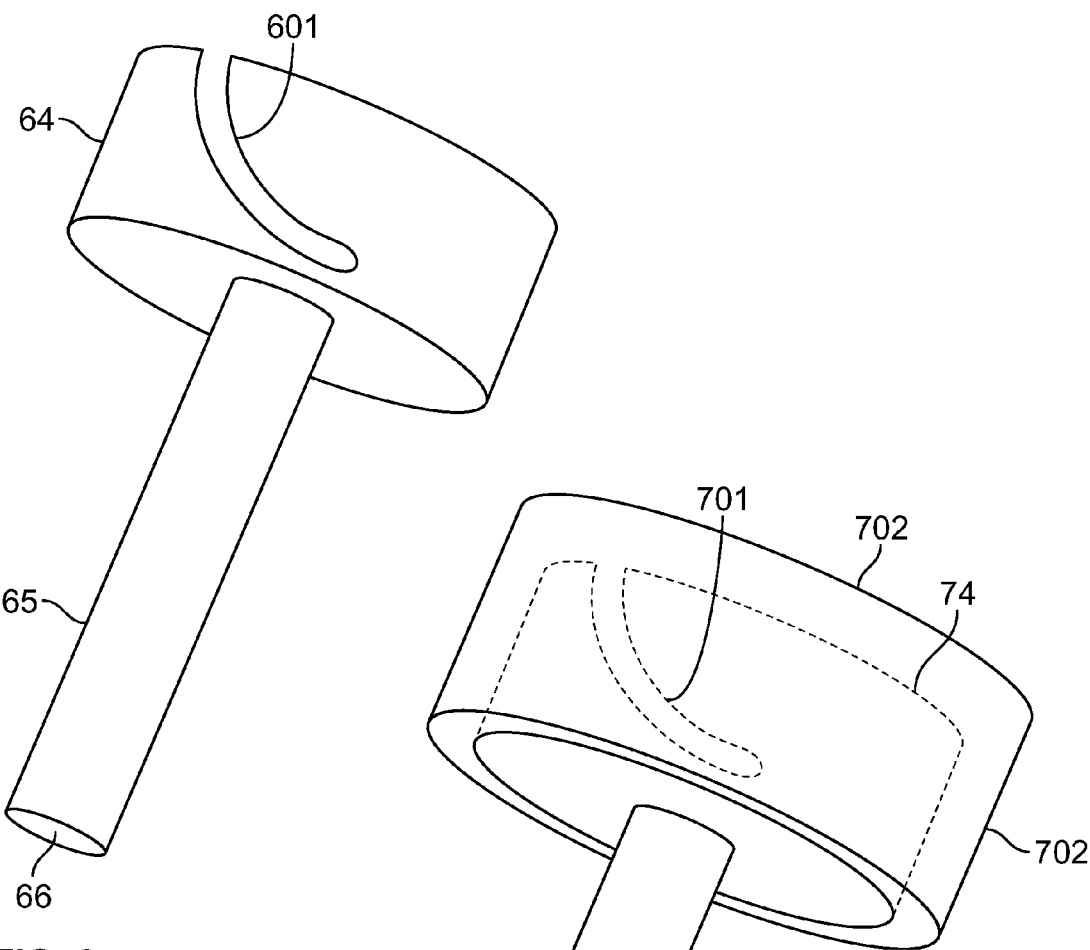
FIG. 6. Sheath hub and sheath, where sheath hub and uncovered groove.
FIG. 7A discloses embodiment where hub has roofless channel.

FIG. 6 discloses sheath hub and sheath, where sheath hub has uncovered groove. What is shown is sheath hub (64), sheath tubular member (or sheath body) (65), distal open end of the sheath (66), and groove (601) of sheath hub (64). In this and other embodiments, distal end of sheath (66) can be open, flared inward, flared outward, closed with a frangible cover, notched, serrated, perforated, configured for attaching a medical device, and so on.

FIG. 7A depicts sheath hub, where sheath hub comprises cover (702) and a groove or channel (701), where cover (702) is external to groove or channel (701). What are shown is groove or channel (701), external cover (702), sheath tubular member (or sheath body) (75), and sheath distal open end (76). Cover (702) can encircle entire sheath hub as shown. Cover (702) can be formed out of the same plastic as sheath hub, or cover (702) can be separately manufactured and attached to sheath hub by an adhesive, by heating, by a snap, by a clip, and the like. Cover (702) can cover or enshroud part of groove or entire groove or channel (701). Cover (702) can encircle or envelope entire hub, or only part of hub. Interior surface (74) of sheath hub is shown and is represented by dashed line.

Figure 7B:
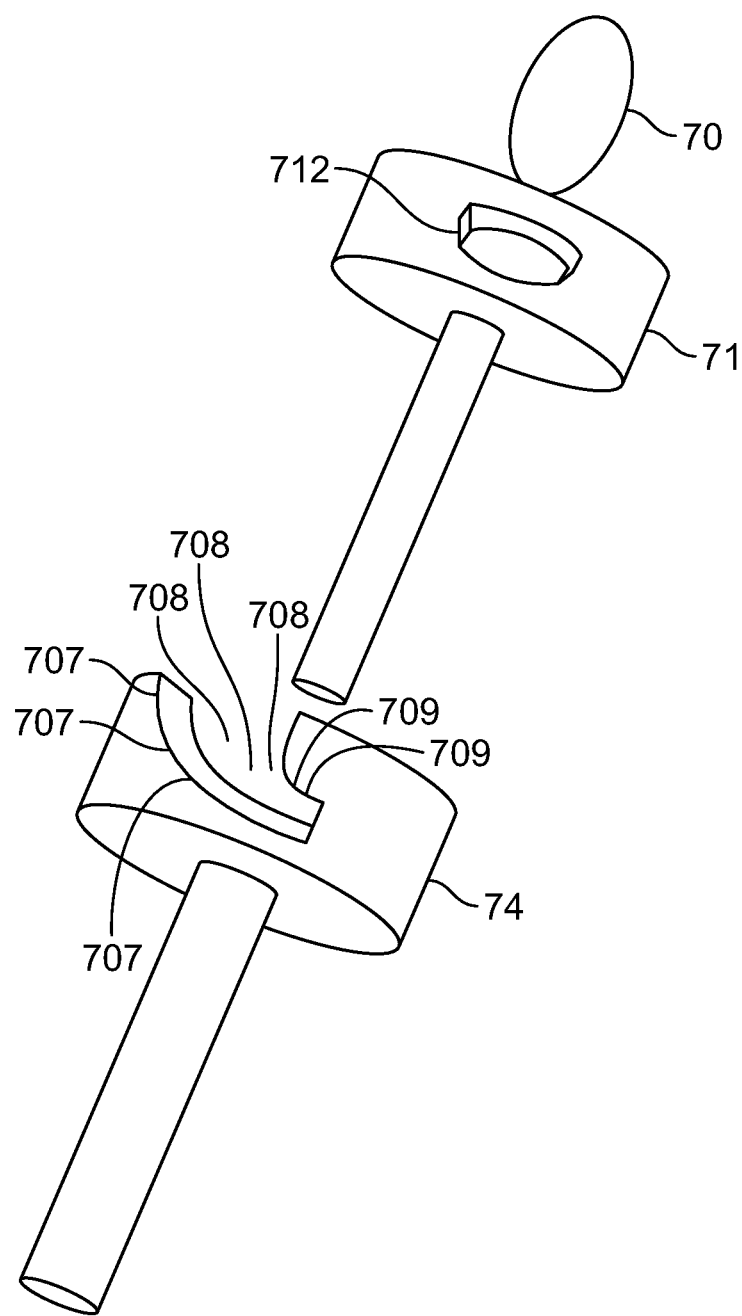
FIG. 7B shows Sheath hub and sheath, where sheath hub comprises a cover and covered groove, where shield is external to groove.

FIG. 7B depicts sheath hub (74) with roofless channel (707, 708, 709), where dilator hub (71) comprises protrusion (712), in this case, a fin or panel. The "rooflessness" can be full or partial. In this case, the channel's rooflessness is partial, where the roofless part is indicated (708), the roofed portion is also indicated (709), and the ventral portion of the channel is (707). In embodiments, what is also provided is dilator hub with a roofless channel, where sheath hub comprises a protrusion. For orientation purposes only, the protrusion and channel may be compared to a snake that crawls downwards through a tunnel. The skilled artisan will realize that the head is distal, the tail is proximal, the snake's spine is dorsal, and the snake's stomach is ventral. The skilled artisan will understand that parts of the tunnel that are nearest to, or that actually contact the snake, can have the same reference names (dorsal; ventral). In the "roofless channel" embodiment, the dorsal surface of the tunnel is partially or completely missing, but the ventral surface of the tunnel is intact. Dilator grip (70) is shown.

In exclusionary embodiments, the present disclosure provides dilator hub or catheter hub with a channel that is fully "roofed" and that is not roofless. Also, provided is dilator hub or catheter hub with a channel that is partially "roofed," that is, a channel that is partially roofless. Also provided is a sheath hub with a channel that is fully "roofed" and that is not roofless. Moreover, what is provided is a sheath hub with a channel that is partially "roofed," that is, a channel that is partially roofless.

Hubs of the present disclosure, include and are not limited to a sheath hub, a dilator hub, a catheter hub, a cannula hub, or to a needle hub, and the like, and can have a circular cross-section, square cross-section, oval cross-section, triangular cross-section, hexagonal cross-section, a cross-section involving zig-zags or fractals, any combination of the above, and the like.

Figure 8:
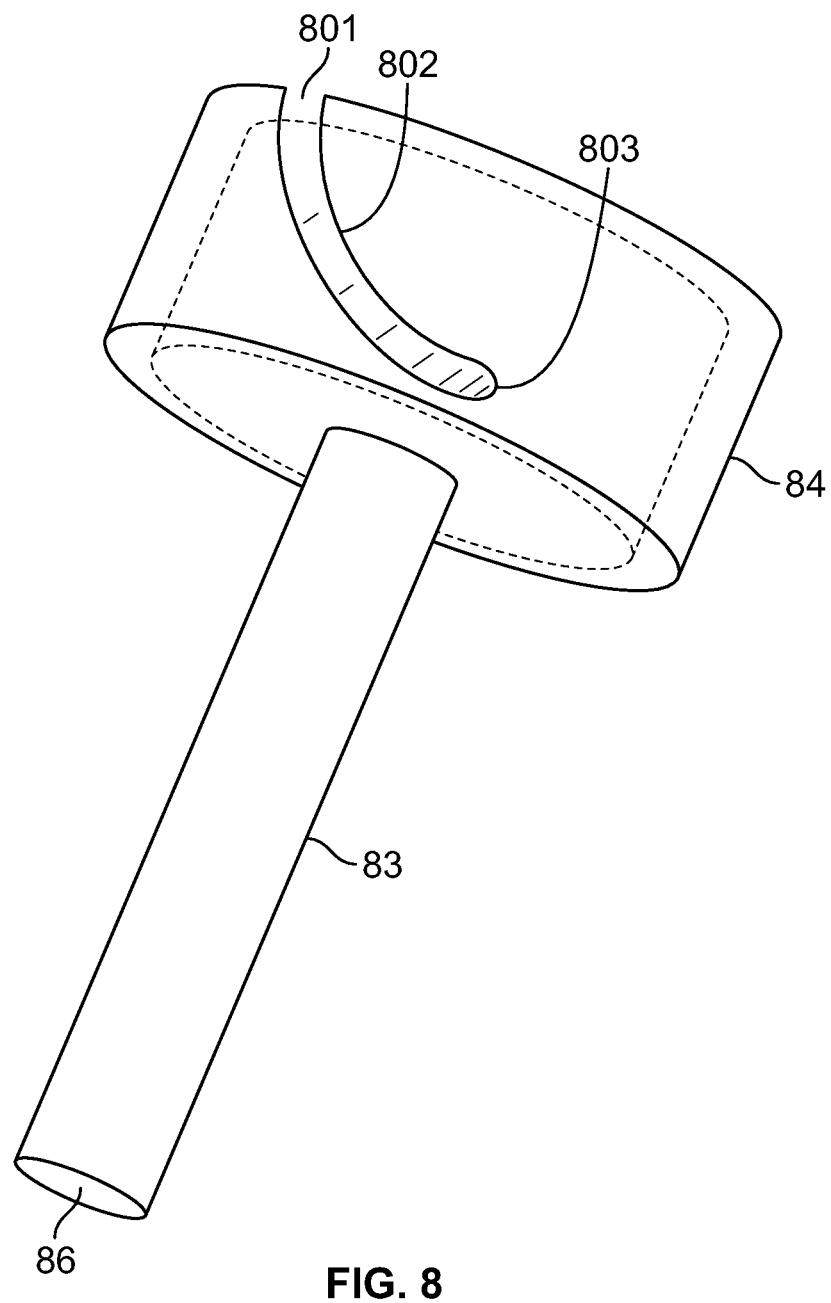
FIG. 8. Sheath hub and sheath, with sheath hub and unshielded groove.

FIG. 8 shows sheath, where sheath hub (84) has uncovered groove (802). What is shown is sheath hub (84), sheath tubular member (or sheath body) (83), sheath distal open end (86), proximal terminus of channel (801), configured for inserting protrusion, e.g., ridge, fin, panel, and the like. Also shown is mid-point of channel (802) and distal terminus of channel (803).

Figure 9:
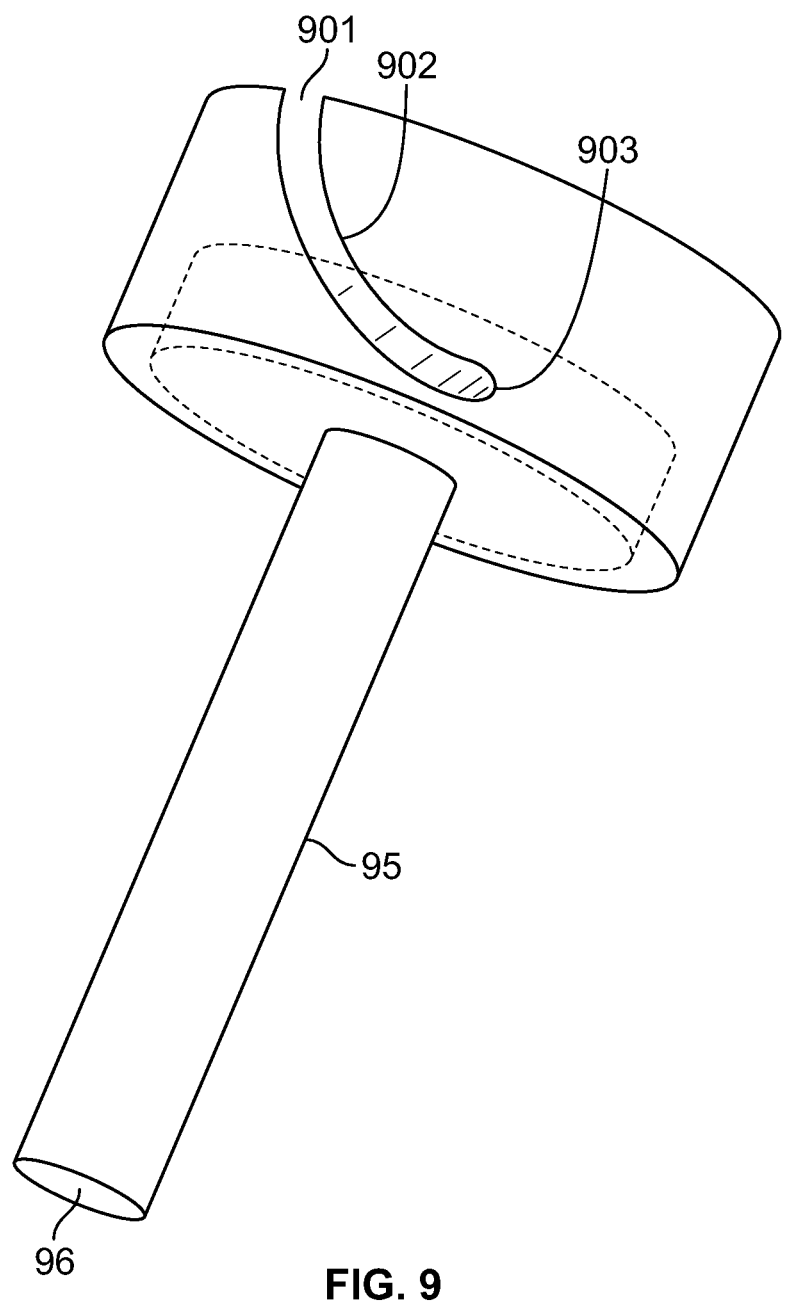
FIG. 9. Sheath hub and sheath, where sheath hub comprises a cover and covered groove, where cover is internal to groove.

FIG. 9 illustrates sheath hub and sheath, where sheath hub comprises cover and covered groove, where cover is internal to groove. In this cover embodiment, and in other cover embodiments, cover can function to prevent dust, solid particles, or fluids from contacting coupling mechanism or locking mechanism. Also, cover can function to ensure that the ridge maintains proper tracking in the groove. The structures include sheath tubular portion (sheath body) (95), sheath distal end (96), start terminus of groove or channel (901), mid-region of groove or channel (902), and end terminus of groove or channel (902). Internal cover is shown in dashed lines.

Figure 10:
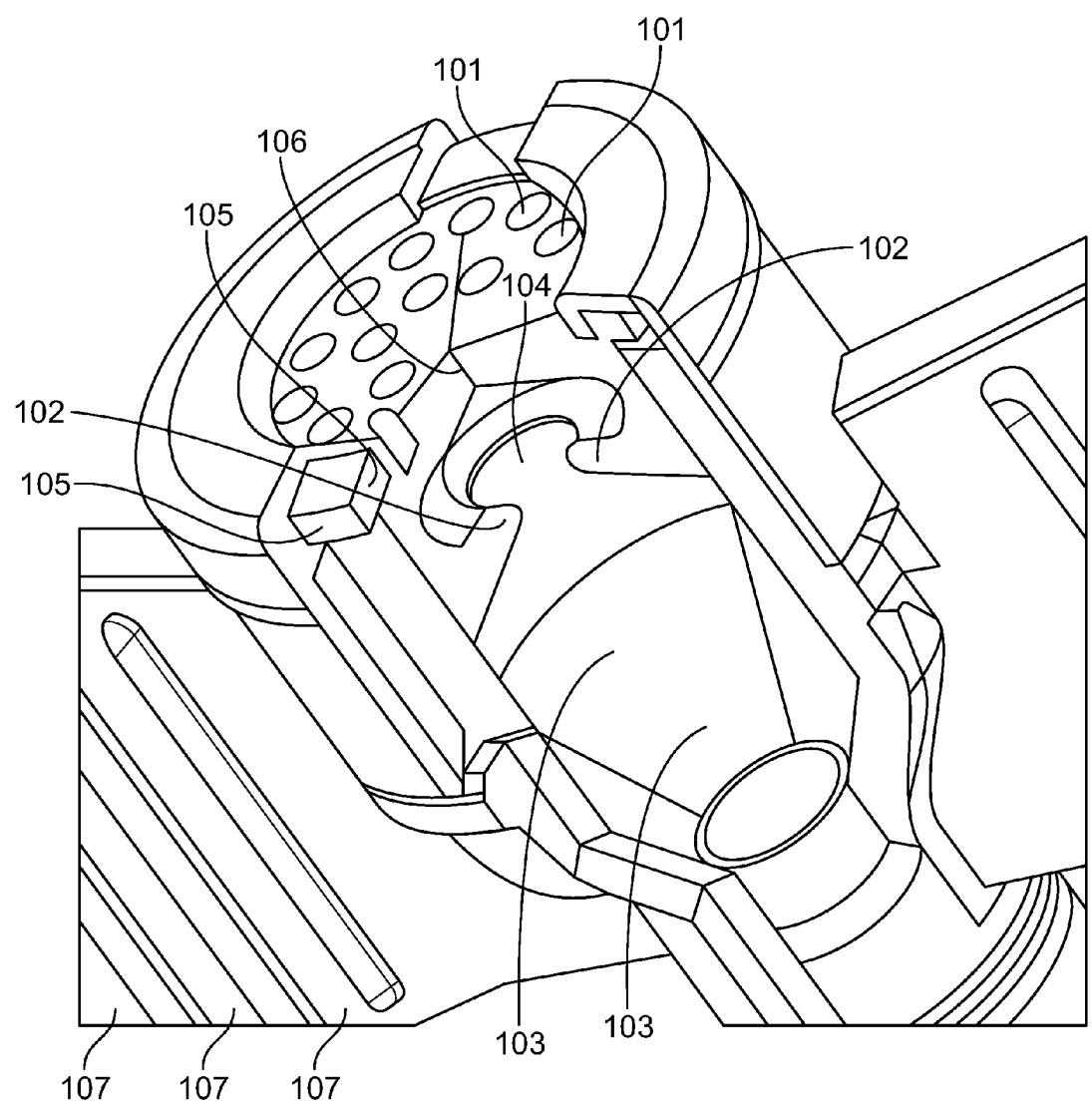
FIG. 10. Valve with seal.

FIG. 10. Valve/seal is provided for one or more embodiments of medical device that comprises valve. The figure discloses outer seal, where outer seal is the first defense against the passage of blood and air. The valve in the figure also contains inner seal, which creates the core hemostatic closure that provides additional support and sealing power. In short, the disclosed valve takes the form of dual hemostatic valve. The figure discloses valve situated in a sheath hub, where proximal part of sheath hub is located in upper left-hand part of the figure, and distal part of sheath hub is situated in lower right-hand part of the figure. With regard to valve, outer seal is situated in the upper left-hand part of the valve (referring to the orientation of the seal in the valve depicted in the diagram, not with respect to the valve itself), while inner seal is situated in the lower right-hand part of the valve.

101 is a plurality of holes. Holes reduce surface tension when inserting a cannula, catheter, dilator, or other medical device, and are configured to provide a sense of softer insertion feel to the user.

102 is inner seal. Inner seal or "secondary seal" or "check valve" provides a circumferential seal around inserted cannula, or around other inserted medical device. An outer seal valve provides a seal when nothing is inserted. Secondary seal is configured for pivoting up and down.

103 is middle cavity. Middle cavity is configured to allow secondary seal to pivot up and down, as a dilator, cannula, or tubular member, is inserted or retracted. The pivoting is like that of a squeegee or wiper, as is understood by the skilled artisan.

104 is through-hole. Through-hole is configured to allow passing of a dilator, cannula, or tubular member, where through-hole is defined by secondary seal.

105 is sealing rib. The sealing rib holds valve in position and tight with cap and hub.

106 is splitting line of splittable valve.

107 is wing, where wing has ridges configured for gripping by fingers.

The disclosure provides a valve/seal, and a sheath that comprises the valve/seal. The valve/seal comprises In embodiments, the disclosure encompasses a medical device, such as a splittable sheath, or a non-splittable sheath, that comprises one or more of: An inner seal that provides a circumferential seal around an inserted cannula; holes that are configured to reduce surface tension when inserting a cannula; a middle cavity configured to allow secondary seal to move up and down; and a seal that privots up and down as a cannula is inserted or retracted.

In an exclusionary embodiments, the present disclosure also excludes any medical device that does not contain the valve/seal. In another exclusionary embodiment, what can be excluded is any medical device, any valve, or any seal, that does not comprise one of the above components. For example, what can be excluded is any device that does not have an inner seal that provides a circumferential seal around an inserted cannula, or any device that does not have holes that are configured to reduce surface tension when inserting a cannula, or any device that does not have a middle cavity configured to allow secondary seal to move up and down. What can be excluded is any device that does not have a seal that pivots up and down as a cannula is inserted or retracted.

In a non-limiting embodiment, valve/seal comprises an outer seal, which is a first defense against the passage of blood and air, and comprises an inner seal that creates the core hemostatic closure that provides additional support and sealing power. A round check valve allows for a seal around the full circumference of the inserted device, for example, a dilator or catheter. A slit allows for a seal when no device is inserted through the valve. Without limitation, the slit can comprise one slit, it can comprise a Y-slit, or it can comprise a star slit. In other aspects, the valve embodiment can exclude a slit that is one slit, exclude a slit that is a Y-slit, or exclude a device that is a star slit.

What is disclosed is point where guidewire is inserted, where dilator is inserted, the peelable sheath extrusion, the position of single slit valve or Y-slit with diameter check valve, the location of thin walls that allow for easy snap and peel. The figure discloses male features that snap into female notches, where the snap-coupling holds two components together after peel. The valve is squeezed in between the two components.

Figure 11:
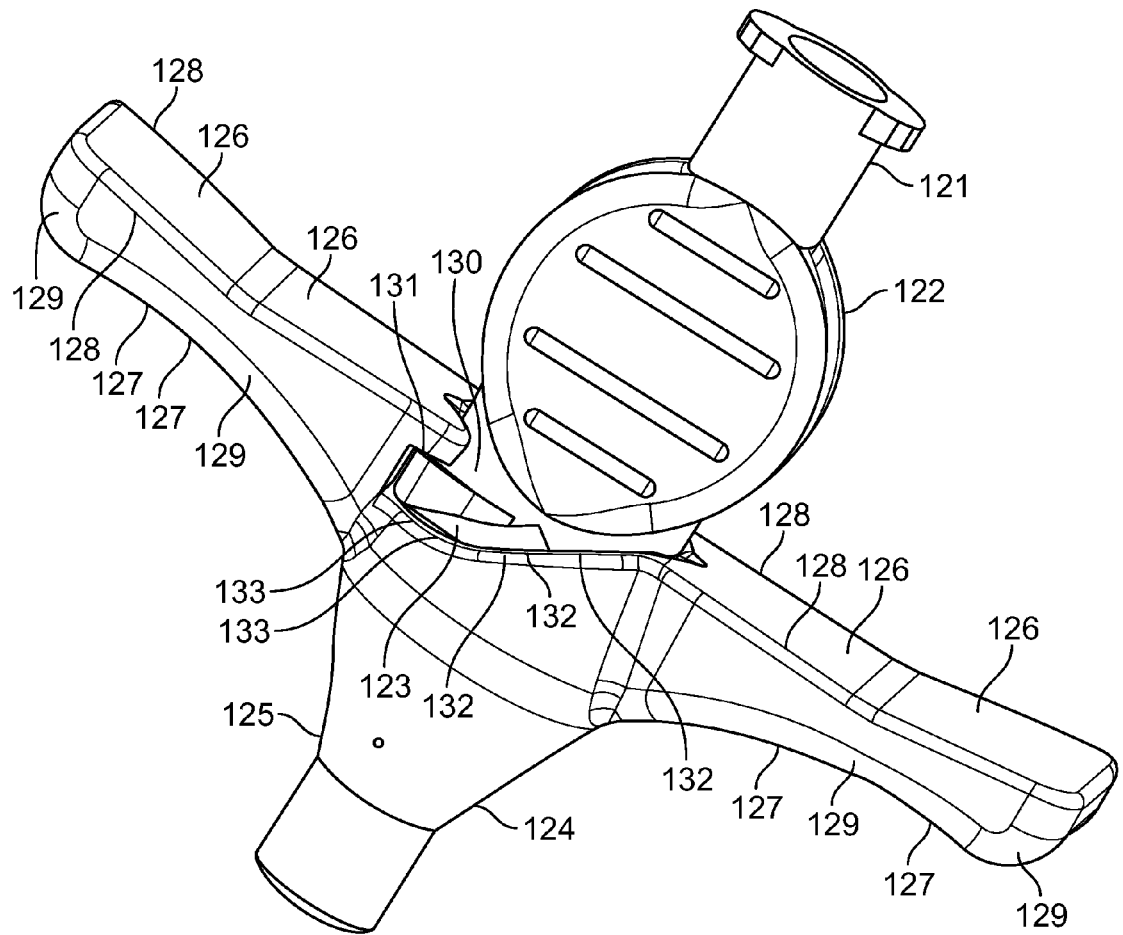
FIG. 11. Dilator inserted into sheath.

FIG. 11 discloses non-valved embodiment. There are two interacting notches that create a tactile locking feel. The present disclosure encompasses embodiments with two or more interacting notches that are configured to create a tactile locking feel, for example, when used by a clinician. In a non-limiting embodiment, the notch flange can pull the dilator hub into the sheath hub, in a function reminiscent to that of a thread. However, the notches are not threads. In a first valved embodiment, the valve can be placed between the dilator hub and sheath hub with a snap cap. In a second valved embodiment, the valved sheath occurs in two pieces, so that the top of the sheath hub (with the wings) remains the same among various different product sizes, while the bottom is interchangeable with a snap feature.

FIG. 11 includes the following. (121) is proximal part of dilator hub. (122) is grip of dilator hub. (123) is fin or panel of dilator hub, located distal to grip. (124) is sheath hub with wings. (125) is distal part of sheath hub. (126) is proximal flat face of wing. (127) is distal face of wing, having concave area configured to fit thumbtip or fingertip. (128) is sharp edge of proximal flat face. (129) is curved face of distal face. (130) is roofless part of channel. (131) is roofed part of channel. (132) is transit of channel where every increment of rotation is accompanied by an increment of movement of dilator hub and sheath hub towards each other. (133) is transit of channel where every increment of rotation is accompanied by an increment of movement of dilator hub and sheath hub away (not towards) from each other. (134) is notch.

Movement Compellable by Notch

In use, where user assembles dilator sheath assembly, and where user exerts only rotational force, only longitudinal force, or a combination of both rotational force and longitudinal force, the notch (combination of 133 transit and of the actual 134 notch), compels movement that slightly increases distance of dilator hub from sheath hub (FIG. 11).

The present disclosure provides one or more of the above components. In embodiments, what is provided is any medical device, e.g., a hub, or a sheath that comprises a hub, or a sheath in combination with a dilator, where sheath comprises a roofless channel that does comprises a notch, and where rotation results in transit of dilator hub towards sheath hub, and where continued rotation in the same rotational direction results in transit of dilator hub away from sheath hub. In this embodiment, transit away occurs in region of channel that is a notch. Roofless channel embodiments, partially roofed channel embodiments, and fully roofed channel embodiments are provided.

Also provided is a medical device, for example, a sheath hub that comprises wings, wherein proximal faces of wings are flat, and distal face of wings are rounded. In an exclusionary embodiment, what can be excluded is a sheath hub that comprises wings, but wherein proximal faces of wings are not flat, and/or wherein distal face of wings are not rounded. Also provided, is sheath hub that comprises wings, wherein distal face of wings is rounded, wherein central area in distal face of wings is concave. In an exclusionary embodiment, what can be excluded is sheath hub with wings, wherein distal face of wings is not concave.

The following concerns exclusionary embodiments. What can be excluded is any medical device, for example a hub, or a sheath that comprises a hub, that does not comprise a roofless channel, that does not comprise a notch, that does not comprise a channel where rotation results in transit of dilator hub towards sheath hub, and where continued rotation in the same direction results in transit of dilator hub away from sheath hub.

Figure 12:
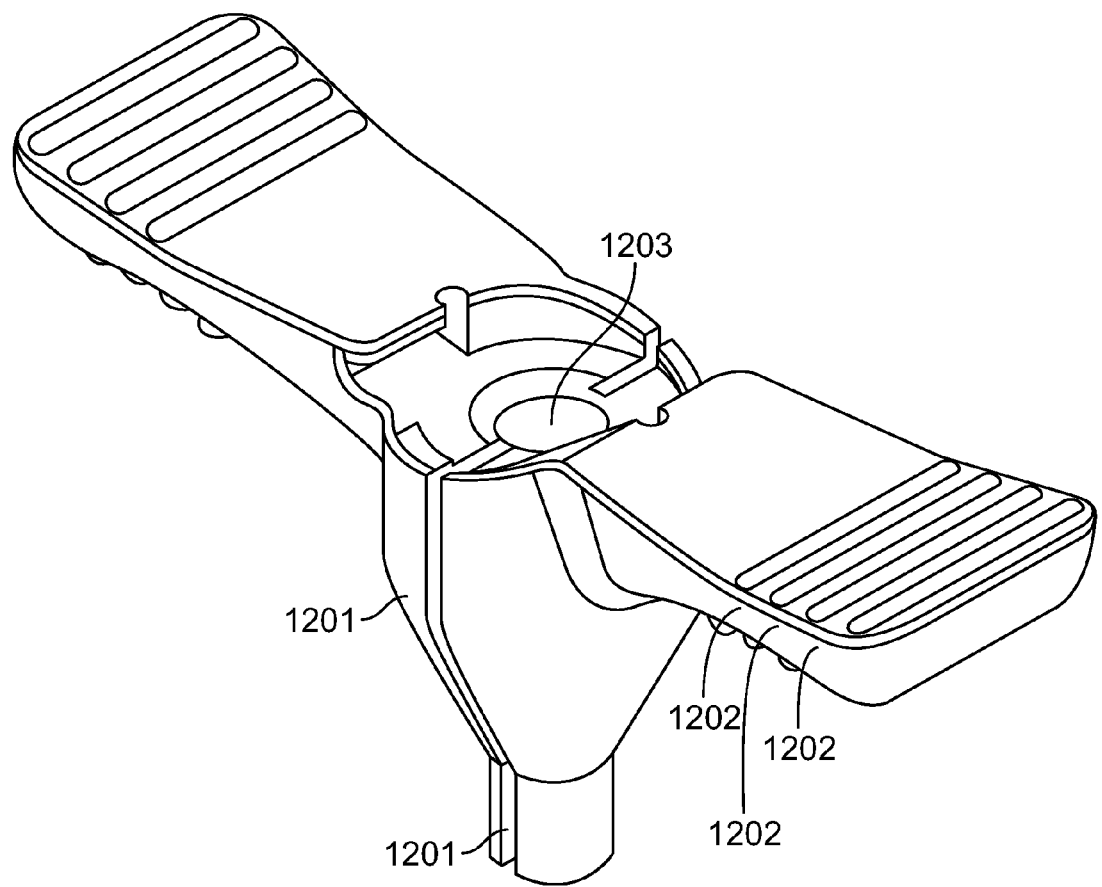
FIG. 12. Hub with wings.

FIG. 12. Hub with wings. 1201 is splittable line of splittable hub. 1202 is wing. 1203 is cavity for valve. Cavity resides below through-hole.

Figure 13:
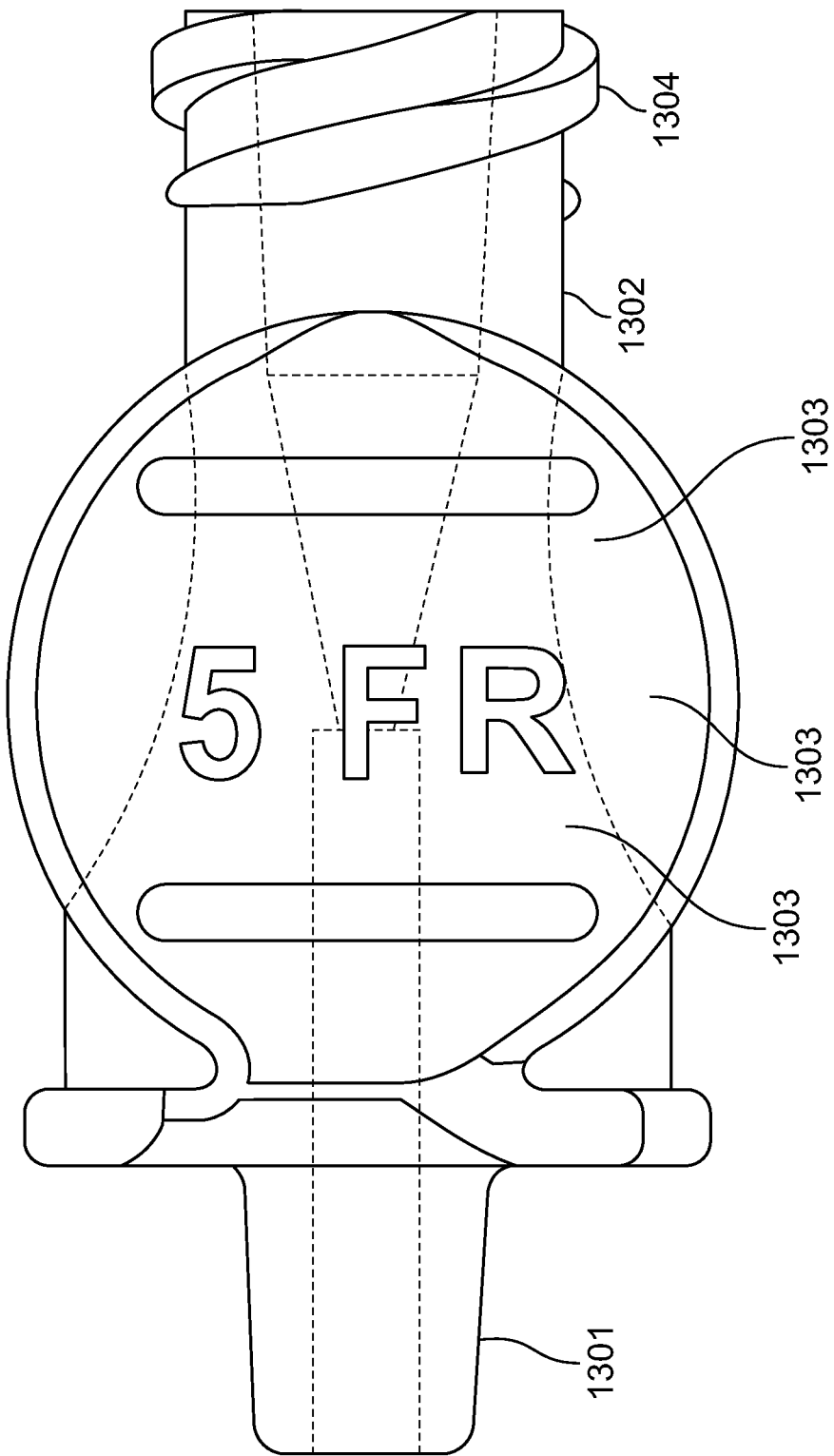
FIG. 13. Side view of hub, viewing face of grip.

FIG. 13. Side view of hub, viewing face of grip. 1301 is distal portion. 1302 is proximal portion. 1302 is flattened face of hub, configured for grasping by thumb and finger. The two opposing flattened faces are somewhat concave, to enhance capacity to be grasped by thumb and finger.

Figure 14:
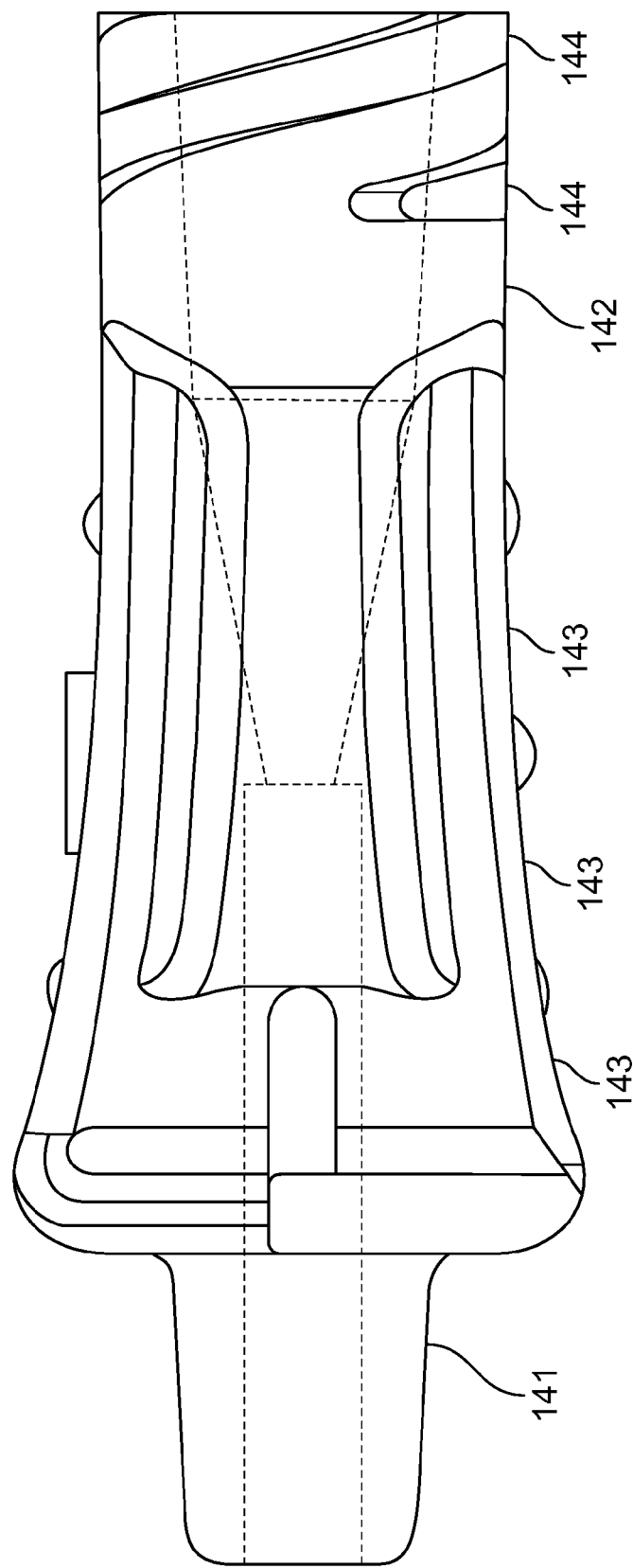
FIG. 14. Side view of hub, viewing edge of grip.

FIG. 14. Side view of hub, viewing edge of grip. 141 is distal portion. 142 is proximal portion. 143 is flattened face of hub (not visible in this view), configured for grasping by thumb and finger. The figure also shows ridges, which reside in between the indicator lines on the drawing.

Figure 15:
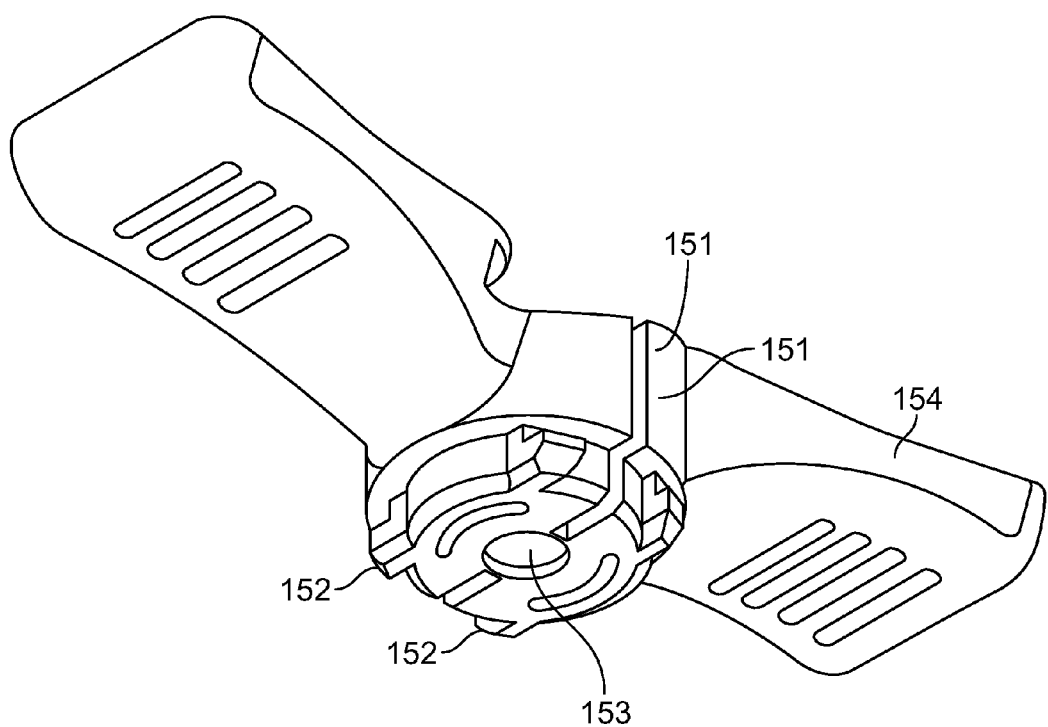
FIG. 15. Three dimensional view of hub, showing wings.

FIG. 15. Three dimensional view of hub, showing wings. 151 is splittable or frangible seam in hub. 152 is male connector for connecting to female connector of sheath hub. 153 is through-hole that is capable of passing cannula or other medical device. 154 is wing.

Figure 16:
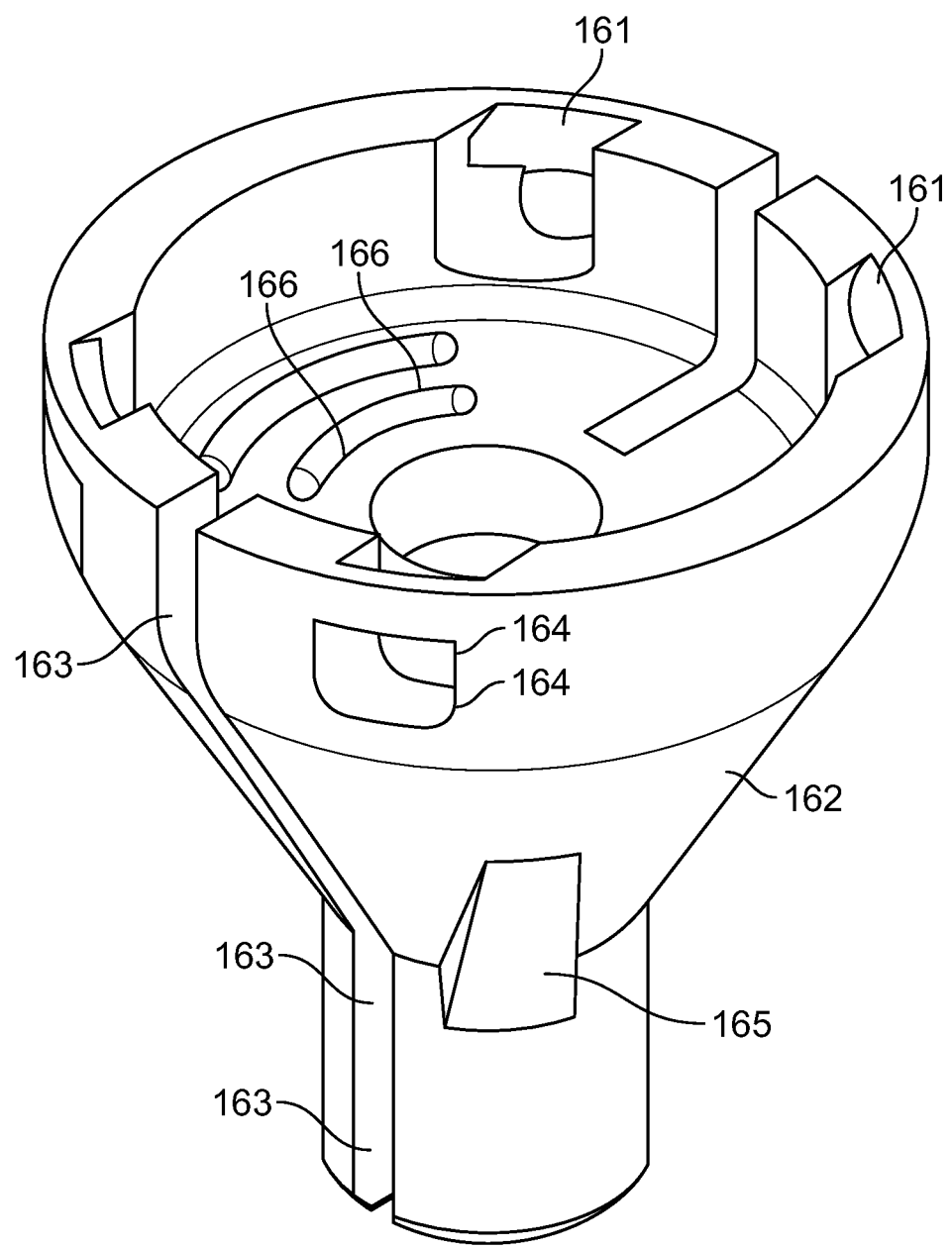
FIG. 16. Three dimensional view of assembly for valve.

FIG. 16. Three dimensional view of assembly for valve. 161 is female snap connector configured to receive splittable hub. The splittable hub carries wings. 162 indicates cavity (not visible) configured to receive valve, filter, or valve and filter. 163 is frangible or splittable seam. 164 is locking tab hole. Locking tab holds cap to hub to allow valve to pinch in between. 165 is rib. Rib provides strength to maintain integrity of device during peeling, that is, during splitting of the valve and the sheath.

Figure 17A:
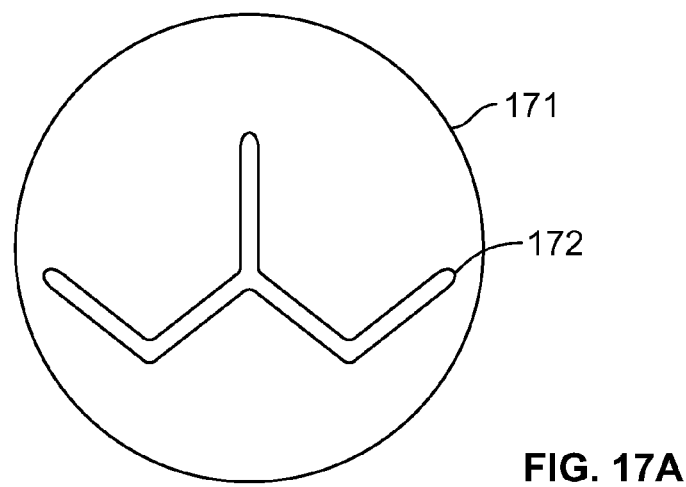
FIGS. 17A, 17B and 17C show valves. Shown is W-valve, equilateral Y-valve, and isosceles Y-valve.
Figure 17B:
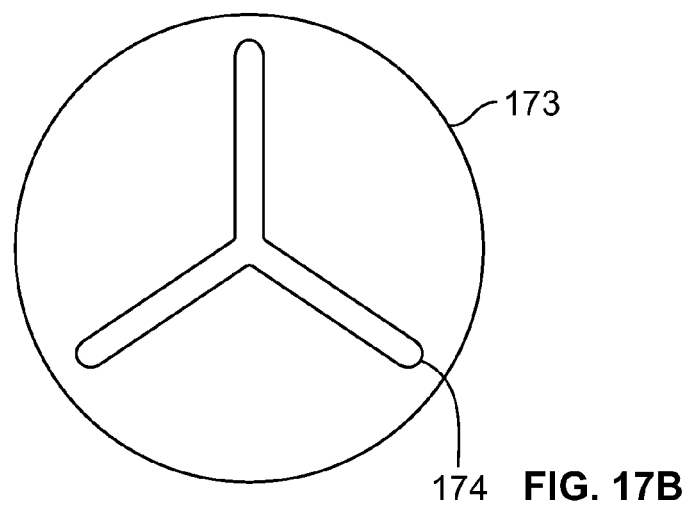
Figure 17C:
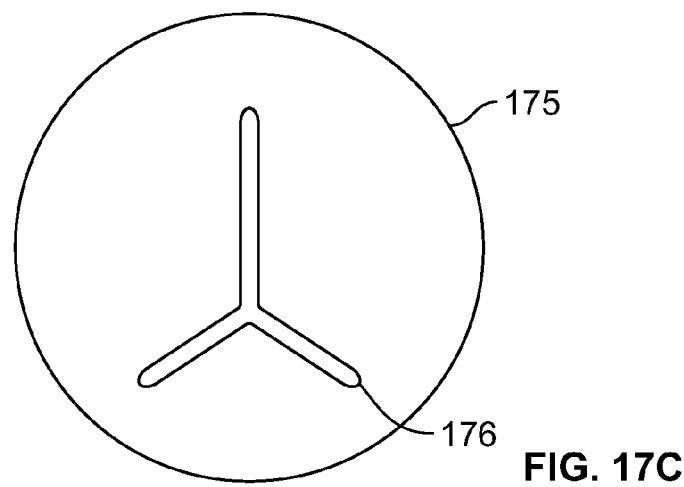

FIG. 17. Valves. Shown is W-valve, equilateral Y-valve, and isosceles Y-valve. 171 is Y-shaped valve. 172 is slit of Y-shaped valve. 173 is Y-shaped equilateral valve. 174 is valve of Y-shaped equilateral valve. 175 is isosceles Y-shaped valve. 176 is slit of isosceles Y-shaped valve. What is also encompassed in the present disclosure is scalene valve. Also encompassed is valve with one linear slit, and embodiments with a plurality of linear slits. The following are exclusionary embodiments. What can be excluded are embodiments that do not have W-shaped valve. What can also be excluded are embodiments that do have a Y-shaped valve. Also, what can be excluded are embodiments that have a scalene valve. What can also be excluded is device with valve having one linear slit, and device with valve having a plurality of slits.

As a general, but non-limiting characteristic of a hemostatic valve slit, the slit is self-closing due to the elasticity of the material used to make the slit, and the slit is able to function as a valve in either direction (it is not a unidirectional valve).

The valve of the present disclosure can be, for example, a straight slit valve, a Y-slit valve, a W-slit valve, an asterisk or star-valve, without limitation. Valve assembly comprising a plurality of valves is contemplated, for example, valves in series or valves in parallel. A straight slit valve is subject to cracking when a round object, such as a guidewire is passed through the straight slit. The Y-slit and W-slit have a lesser tendency, or no tendency, to crack, as compared to the tendency of the straight slit. W-slit is similar in conformation to Y-slit, but the W-slit contains an extra slitted region that may be called a "flare." The present disclosure encompasses a W-slit valve with a reduced risk for cracking when compared to a straight-slit valve, and with superior splittability when compared to a Y-valve.

W-slit embodiment of the valve is shown (top view). W-slit is structurally unique, in that two edges of valve are weakened somewhat to promote better splitting of valve, that is, splitting or peeling when removing device from patient's body. What is disclosed encompasses valve assembly comprising a W-slit valve; valve assembly comprising W-slit valve and sheath; valve assembly comprising W-slit valve and sheath, wherein in use better splitting occurs in comparison to a valve assembly comprising a Y-slit valve and a sheath. In this context, "better splitting" refers to more rapid splitting, cleaner splitting, splitting with less wayward split lines, splitting with lesser attention to placement of fingers and thumb, for example, when working under conditions of emergency surgery and the like, as compared for example, with a Y-slit valve. Guidance for measuring and quantitating fragments and splitting, and the ability to break cleanly, in the context of plastics, is available from, e.g., U.S. Pat. Nos. 5,500,260 issued to Halle et al, and 5,001,935 of Takkanat et al, each of which is incorporated herein by reference in their entirety.

W-slit embodiment of valve is shown (side view), showing relative, non-limiting distances, of the indicated segments or regions of the slit, where these regions may be called, neck, forearm, and arm. The full diameter of valve is diameter D. In one aspect, the width of W-slit (in direction of span of forearm and arm) is less than 99% of D, less than 98% D, less than 97% D, less than 96% D, less than 95% D, less than 90% D, less than 85% D, less than 80% D, less than 75% D, less than 70% D, and the like. In another aspect, the width of the W slit is about 99% of D, about 98% D, about 97% D, about 96% D, about 95% D, about 90% D, about 85% D, about 80% D, about 75% D, about 70% D, and the like. The region consisting of the forearm and arm (but excluding the neck) has a height H. In one aspect, H is about 50% D, about 45% D, about 40% D, about 35% D, about 30% D, about 25% D, about 20% D, about 15% D, or about 10% D. In another aspect, H is 45-50% D, H is 40-45% D, H is 35% 40% D, 30-35% D, 25-30% D, 20-25% D, 15-20% D, 10-15% D, and the like.

FIG. 18 discloses a view of radial end of wing, as viewed from an infinite distance radially away from wing. FIG. 18A shows vertical leading edge and vertical trailing edge. FIG. 18B shows angled leading edge, and angled trailing edge. FIG. 18C shows vertical leading edge and vertical trailing edge. FIG. 18D shows angled leading edge and angled trailing edge.

Figure 18A:
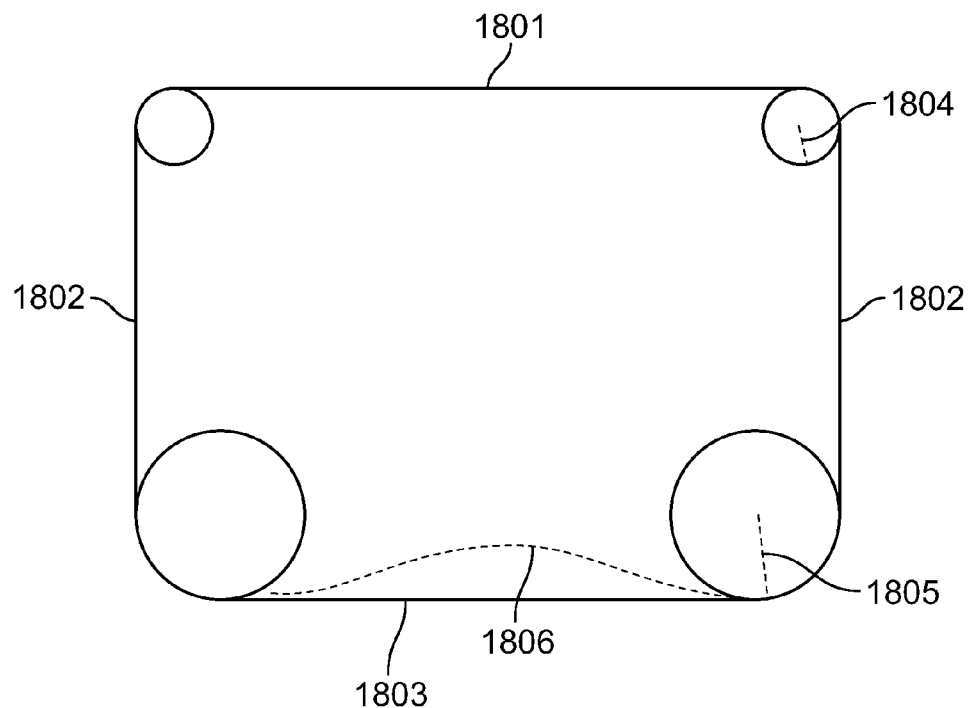
FIGS. 18A, 18B, 18C and 18D show edges, and faces of wings.
Figure 18B:
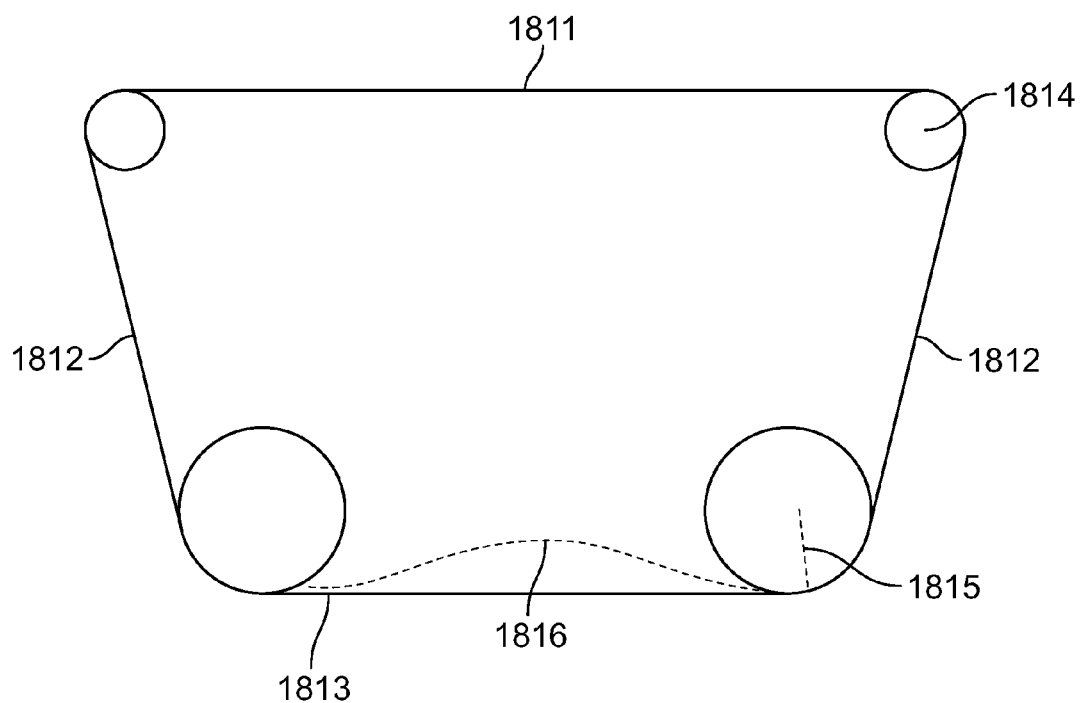
Figure 18C:
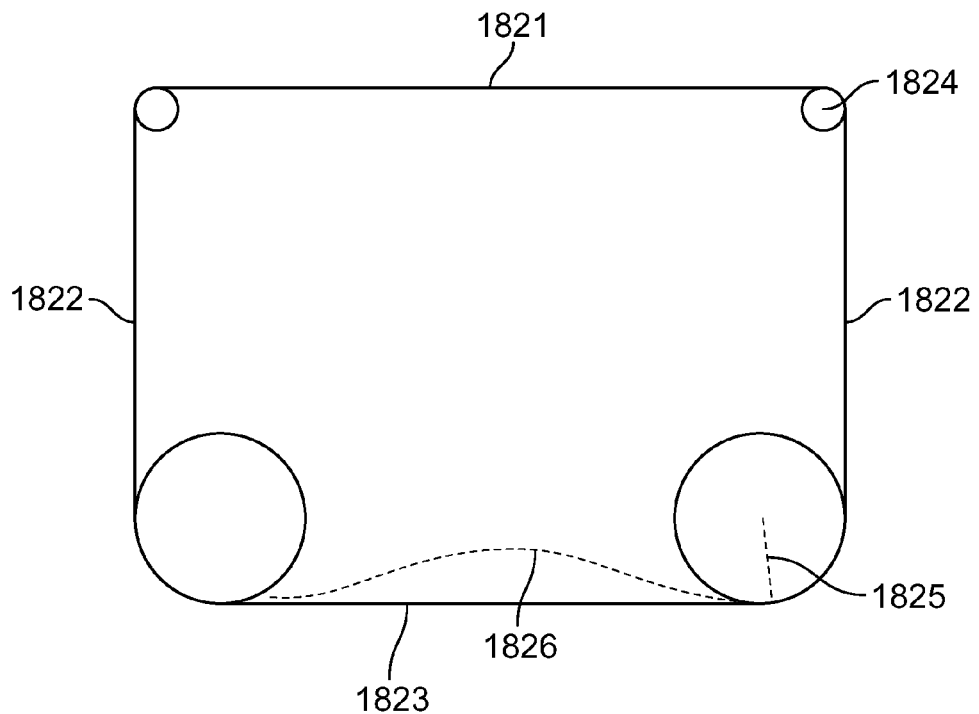
Figure 18D:
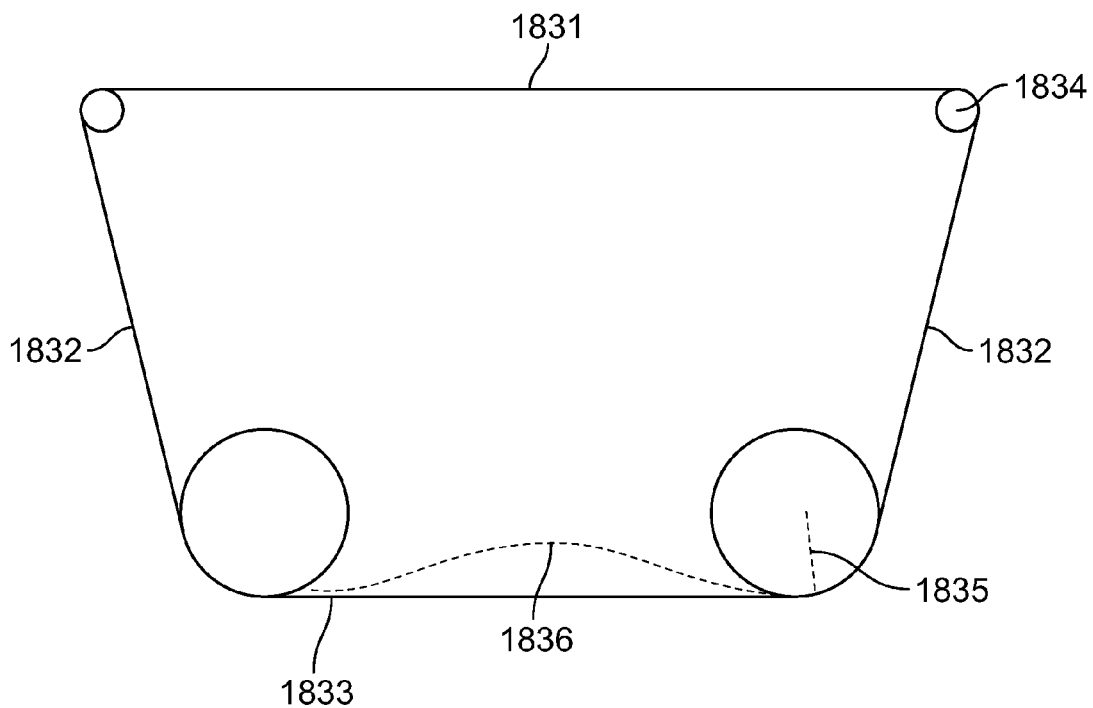

FIG. 18A and FIG. 18A have relatively blunt edges on upper face. FIG. 18C and FIG. D have relatively sharp edges on upper face.

1801 is proximal flat face. 1803 is distal rounded face. 1802 refers to leading edge or to trailing edge. The term leading edge refers to the edge, during twisting (screwing motion) insertion of dilator into sheath, that confronts air pressure. Trailing edge is the edge that does not confront air pressure, during insertion. 1804, 1805, 1814, and 1815, refer to imaginary radius, or best-possible estimate of radius, of edge. These structure numbers can be used to identify sharpness or bluntness of edges. 1806, 1816, 1826, and 1836, refer to concave lower face of wings. 1812, 1822, and 1832, also refer to leading edge and to trailing edge, as indicated.

What is provided is a medical device where lower surface of wings or tabs is concave. Also, what is provided is a medical device where one or both of leading edge and trailing edge is vertical. Also, the disclosure encompasses a medical device where one or both of leading edge and trailing edge is angled. The angles of the leading edge and trailing edge, with respect to each other, can have the same, or similar, configuration as depicted by the profile of an upright ice cream cone, or by the angles of a profile of a conical hat that is worn, or any combination thereof.

In exclusionary embodiments, what can be excluded is any medical device, or any sheath that has wings (alternatively known as tabs), that do not possess one or more of the indicated structures. For example what can be excluded is a medical device where lower face does not have a concave surface. Also, what can be excluded is medical device where one or both leading edge and trailing edge are not vertical. Also, what can be excluded is medical device where one or both leading edge and trailing edge are not angled.

The present disclosure encompasses the following. Sheath hub and wings are shown, for one non-limiting embodiment. The location of the top flat and wing angle to the underside concave profile (including finger grips) results in a superior ergonomic fit. Recessed sheath hole creates a place for the user's thumb to securely seal hole. Hole can be sealed either with the left thumb, or with the right thumb. Top edge of wings have a sharper edge, as compared to the underside of the wings, which have a blunter edge. This creates smooth grip on the underside and better leverage for peeling on the top side. In other words, what is created is a superior ergonomic fit as compared, for example, to embodiments where the top edge is blunter and underside edge is sharper. The relative sharpness of the upper edge and bluntness of the lower edge are expressed in numbers. The radius of the upper edge is less than $1/10^{th}$ of an inch, less than $1/20^{th}$ of an inch, less than $1/50^{th}$ of an inch, less than $1/100^{th}$ of an inch, under $1/500^{th}$ of an inch, under $1/1000^{th}$ of an inch, less than $1/2000^{th}$ of an inch, below $1/4000^{th}$ of an inch, below $1/5000^{th}$ of an inch, under $1/10,000^{th}$ of an inch, and the like. The radius of the upper edge is greater than, for example, $1/50^{th}$ of an inch, greater than $1/25^{th}$ of an inch, greater than $1/20^{th}$ of an inch, greater than $1/15^{th}$ of an inch, greater than $1/10^{th}$ of an inch, more than $1/8^{th}$ of an inch, more than $115^{th}$ of an inch, and the like.

Predetermined combinations of the above dimensions are provided, for example, wherein the upper edge has a radius of less than $1/100^{th}$ of an inch and the lower edge has a radius of more than $1/20^{th}$ of an inch, upper edge is has a radius of less than $1/100^{th}$ of an inch and the lower edge has a radius of more than $1/10^{th}$ of an inch, wherein the upper edge is has a radius of less than $1/1000^{th}$ of an inch and the lower edge has a radius of more than $1/20^{th}$ of an inch, upper edge is has a radius of less than $1/1000^{th}$ of an inch and the lower edge has a radius of more than $1/10^{th}$ of an inch, wherein the upper edge is has a radius of less than $1/100^{th}$ of an inch and the lower edge has a radius of more than $1/6^{th}$ of an inch, upper edge is has a radius of less than $1/1000^{th}$ of an inch and the lower edge has a radius of more than $1/6^{th}$ of an inch, wherein the upper edge is has a radius of less than $1/10,000^{th}$ of an inch and the lower edge has a radius of more than $1/6^{th}$ of an inch, and the like.

Thus, the disclosure provides sheath hub that contains sheath hole, where sheath hole (in use) is configured for the user's thumb to seal sheath hole. In some aspects, the disclosure provides sheath hub encompassing wings, where wings have top edge and under edge, wherein top edge is sharper than under edge, thereby providing a smoother grip and better leverage for peeling. The smoother grip and better leverage for peeling is with respect to, an embodiment where top edge and under edge do not have a different sharpness, or where upper edge is relatively blunt and underside edge is relatively sharp.

Intermittent Configuration of Ridge (Protrusion, Male Thread) as Disclosed in FIGS. 13 and 14

Ridge is intermittent, where ridge is reduced in radial extent, or non-existent in radial extent. The reduced or non-existent parts of ridge enables the molding process, or is required for an efficient molding process during manufacturing. That is, the reduced or non-existent parts of intermittent ridge enables pulling apart of the two halves of the mold. The part of the intermittent ridge where the ridge is non-existent is the "flat" part of the ridge. The non-existent parts of ridge can alternatively be described as parts that are measurable, but where measurements reveal that the radial dimension of the ridge is extremely small or infinitely small. The "flat" part resembles a part of the hub that has been shaved off, but the flatness does not actually result from any shaving, but instead is produced in the flat configuration in the mold. (The device, in other aspects, can include a dilator hub where the flat area is the result of shaving or cutting.) The configuration described next is the part of the ridge that is not flat. Thus, in viewing the dilator hub longitudinally, and from the proximal-to-distal direction, the ridges are intermittent, where the ridges are prominent and substantially constant in radial dimension (dimension extending from imaginary central axis in a radial direction). The present disclosure encompasses the following. What is shown above same view of dilator hub, but where dilator is rotated by 90 degrees, so that the French size symbol faces upwards (or faces downwards).

In an exclusionary embodiment, what can be excluded is a device, a hub, a sheath, and so on, where thread does not have an intermittent structures, or where thread does not have an intermittent configuration.

The present disclosure provides dilator hub comprising ridge (protrusion, male thread) configured for coupling with sheath hub, wherein ridge is intermittent, and includes at least one "first region" where the ridge is minimal, reduced, or non-existent, and at least one "second region" where ridge is dimensioned to have a substantially constant radius, and dimensioned to fit couplingly into groove of sheath hub. The "first region" of the ridge is defined as the sum of all minimal, reduced, or non-existent parts of the ridge, in a given 360 degree arc around the axis. The "second region" of the ridge is defined as the sum of all maximally-dimensioned (radial dimension) parts of the ridge, in the same given 360 degree arc around the axis.

The curved profile allows for thumb-index finger grip. The side material is thin to create equal walls to prevent molding issues. In detail, thin walls promote equivalent cooling among any plurality of walls during molding, that is, the thin walls reduce the risk of unequal cooling with adverse structural consequences. In some embodiments, the ridge is not a thread, while in other embodiments, the ridge is a thread. The symbol designating French size acts as grip point. In one embodiment, each wing comprises a vertical rib which has a place to lock or couple into the sheath hub, where the lock rib is configured to strengthen each wing. The dilator nose, that is, distal dilator tip, is tapered for easy mold release and tight fit into sheath internal diameter (ID) feature. The nose helps lead into sheath internal diameter (ID).

A side view of dilator hub is shown. The orientation of dilator hub is such that the distal part of the dilator hub resides at the left-hand part of the figure, while the proximal part of the dilator hub resides at the right-hand part of the figure. The side view of grip of dilator hub shows a greater width (at left-hand part of figure) and a lesser width (at right-hand part of figure), where these relative widths are configured to fit the contour of user's thumb and fingers. The following concerns the ridge where, as mentioned above, the ridge has portion that is flat, minimal, or non-existent, as well as a portion that is of maximal radius, and where the maximal radius is of a substantially constant radius. In this figure, the top edge of the figure reveals the flatness of the flat ridge portion. In other words, in this orientation, intermittent ridge cannot be seen as extending beyond either of the faces of the grip, where the reason is that in this orientation, intermittent ridge does not extend, or only minimally extends, beyond either of the faces of the grip.

Sheath hub with wings is shown. Where the wings define a diameter axis that is perpendicular to the longitudinal axis of the sheath body, and where this diameter axis consists of two opposing radial axes, this view is from the far-radial end of the first radial axis towards the second radial axis.

Peel-away sheath valve body subassembly is shown. Valve that fits into the valve body subassembly is not shown here, but instead is revealed in subsequent figures. This component can, in some embodiments, include a peel-away extrusion over-molded by the valve body, which also provides a nose to press-fit a removable plastic guard tube. The body has female features which allow male features at the final assembly to permanently snap together. The inner valve seat has male features (peaks, squares, or pegs) which provide grip for the valve to compress tightly for a seal at final assembly with peel-away sheath wing cap. The valve grips also will grip the valve in tension when the device is peeled apart.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

While methods, devices, compositions, and the like, have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims. It is understood that the term, present disclosure, in the context of a description of a component, characteristic, or step, of one particular embodiment of the disclosure, does not imply or mean that all embodiments of the disclosure comprise that particular component, characteristic, or step.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/ these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC §132 or other such laws— to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible.

What is claimed is:

1. A sheath assembly, comprising:
    a sheath member comprising:
        a sheath tubular member that defines a first longitudinal axis and that has a sheath inner diameter and a sheath outer diameter, and
        a sheath hub proximal of the tubular member; and
    a tubular member comprising:
        a dilator, cannula or catheter that defines a second longitudinal axis and has a first outer diameter,
        a dilator hub proximal of the dilator, and
        a grip connected to the dilator hub to be grasped by a practitioner,
    wherein:
        the dilator hub comprises at least one dilator protrusion that extends radially outwards with respect to the second longitudinal axis, and the sheath hub comprises at least one sheath channel, the at least one dilator protrusion and the at least one sheath channel being configured to reversibly and rotatingly couple to one another, wherein the at least one sheath channel extends in a sheath arc having a predetermined number of degrees, the at least one sheath channel being configured to guide the dilator hub to move rotatably in said sheath arc, and to guide the at least one dilator protrusion of the dilator hub to move in a proximal to distal direction along the second longitudinal axis by holding the sheath hub in a stationary position and concurrently rotating the dilator hub, or the sheath hub comprises at least one sheath protrusion that extends radially inwards with respect to the first longitudinal axis, and the dilator hub comprises at least one dilator channel, the at least one sheath protrusion and at least one dilator channel being configured to reversibly and rotatingly couple to one another, wherein the at least one dilator channel extends in a dilator arc having a predetermined number of degrees, the at least one dilator channel being configured to guide the at least one sheath protrusion of the sheath hub to move rotatably in said dilator arc, and to guide the sheath hub to move in a distal to proximal direction along the first longitudinal axis by holding the dilator hub in a stationary position and concurrently rotating the sheath hub.

2. The sheath assembly of claim 1, wherein the at least one dilator protrusion or the at least one sheath protrusion comprises at least one ridge, at least one fin, at least one panel, or at least one male thread.

3. The sheath assembly of claim 1, wherein the at least one dilator protrusion or the at least one sheath protrusion comprises only one ridge, only one fin, only one panel, or only one male thread.

4. The sheath assembly of claim 1, wherein the sheath member and the tubular member are not coupled to each other when contained by a package.

5. The sheath assembly of claim 1, wherein maximal insertion of the dilator, cannula or catheter into the sheath tubular member is accomplished by transit of the at least one dilator protrusion through the at least one sheath channel by a relative rotation of X degrees between the dilator hub and the sheath hub.

6. The sheath assembly of claim 5, wherein the transit comprises a sequential first transit and second transit, wherein an inflection point or central location of an inflection region is between the first transit and the second transit, and wherein rotation during the first transit is about 0.5 X degrees and rotation during the second transit is about 0.5 X degrees.

7. The sheath assembly of claim 5, wherein longitudinal movement of the dilator hub towards the sheath hub during the first transit is greater than longitudinal movement of the dilator hub towards the sheath hub during the second transit.

8. The sheath assembly of claim 5, wherein the relative rotation of X degrees to achieve maximal insertion is less than 180 degrees.

9. The sheath assembly of claim 1, wherein rotational movement of the dilator hub relative to the sheath hub results in longitudinal movement of the dilator hub relative to the sheath hub.

10. The sheath assembly of claim 1, wherein the sheath hub comprises a hemostasis valve, and wherein the hemostasis valve comprises a W slit.

11. The sheath assembly of claim 1, wherein:

the sheath tubular member is a peel away sheath comprising a first longitudinal half and a second longitudinal half, the first longitudinal half being separable from the second longitudinal half, the sheath hub further comprises two opposing tear away wings, one tear-away wing on the side of the first longitudinal half, the other tear-away wing on the side of the second longitudinal half, and wherein simultaneous application of axial force on the first tear-away wing in opposite vector direction as axial force on the second tear-away wing results in separation of the first longitudinal half from the second longitudinal half.

12. The sheath assembly of claim 1, wherein the sheath member further comprises a hemostasis valve that has a plurality of holes configured to reduce surface tension when inserting the dilator, cannula or catheter, the hemostasis valve comprising:

an inner seal configured to provide a circumferential seal around the dilator, cannula or catheter, an outer seal valve configured to seal the sheath member when the dilator, cannula or catheter is not inserted, a secondary seal configured to pivot up and down, a middle cavity configured to allow the secondary seal to pivot up and down, as the dilator, cannula or catheter is inserted or retracted, and a through-hole configured to allow passing of the dilator, cannula or catheter, where the through-hole is defined by the secondary seal.

* * * * *